(12) United States Patent
Carey et al.

(10) Patent No.: US 6,432,359 B1
(45) Date of Patent: Aug. 13, 2002

(54) REAGENT HANDLING SYSTEM AND CONFIGURABLE VIAL CARRIER FOR USE THEREIN

(75) Inventors: Glen A. Carey, Grafton; Scott E. Mathis, Bay Village; David P. Weber, Strongsville, all of OH (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/484,955

(22) Filed: Jan. 18, 2000

Related U.S. Application Data

(63) Continuation of application No. 09/099,368, filed on Jun. 18, 1998, now Pat. No. 6,066,300, which is a continuation-in-part of application No. 08/742,014, filed on Oct. 31, 1996, now Pat. No. 5,788,928, which is a continuation of application No. 08/499,271, filed on Jul. 7, 1995, now Pat. No. 5,609,822.

(51) Int. Cl.[7] ............................................. B01D 35/00
(52) U.S. Cl. ........................ 422/63; 422/102; 422/104
(58) Field of Search .............................. 422/63, 65, 67, 422/100, 102, 104

(56) References Cited

U.S. PATENT DOCUMENTS 5,525,304 A * 6/1996 Matsson et al. ............ 422/104
5,672,317 A * 9/1997 Buhler et al. ................ 422/65

* cited by examiner

*Primary Examiner*—Matthew O. Savage
(74) *Attorney, Agent, or Firm*—Weingarten, Schurgin, Gagnebin & Lebovici LLP

(57) ABSTRACT

A vial carrier having plural reagent compartments disposed linearly along the length of the carrier. Each compartment is adapted for receiving one of plural reagent vials. The carrier is provided with indicia uniquely identifying it to an automated assay device. Similarly, each compartment of the carrier has associated with it indicia which are at least unique to the particular carrier. Lastly, each vial installable within a carrier compartment has indicia unique to the contents of the vial. A film seal is applied to the vial opening prior to an integrated cap/seal assembly for the purpose of ensuring that the assembly is liquid-tight. The carrier is configured to be disposed on a slide of an inclining tray within an enclosure. Data reflecting which vial is located in which compartment of a given carrier is collected and provided to the automated instrument prior to installation of the carrier into the enclosure. The automated instrument has, associated with the enclosure, an indicia recognition element to identify each installed carrier. In this manner, the instrument has information reflecting that a desired vial is installed in a particular compartment of a carrier which is installed on a particular slide within the enclosure.

5 Claims, 20 Drawing Sheets

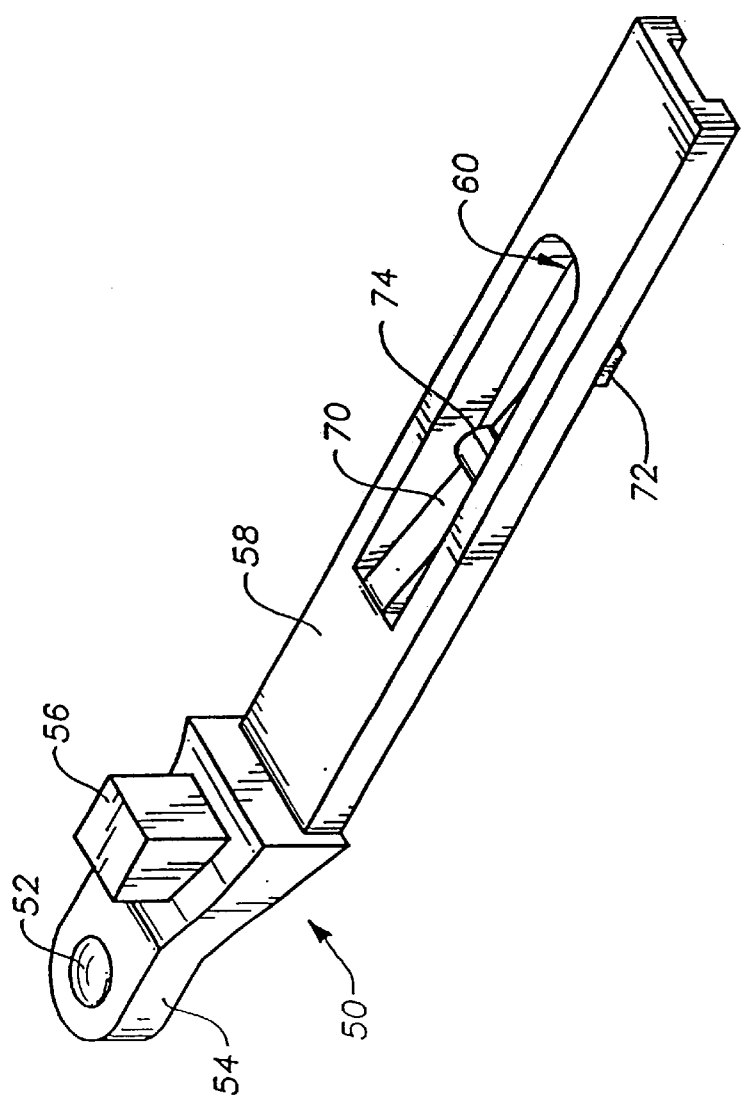
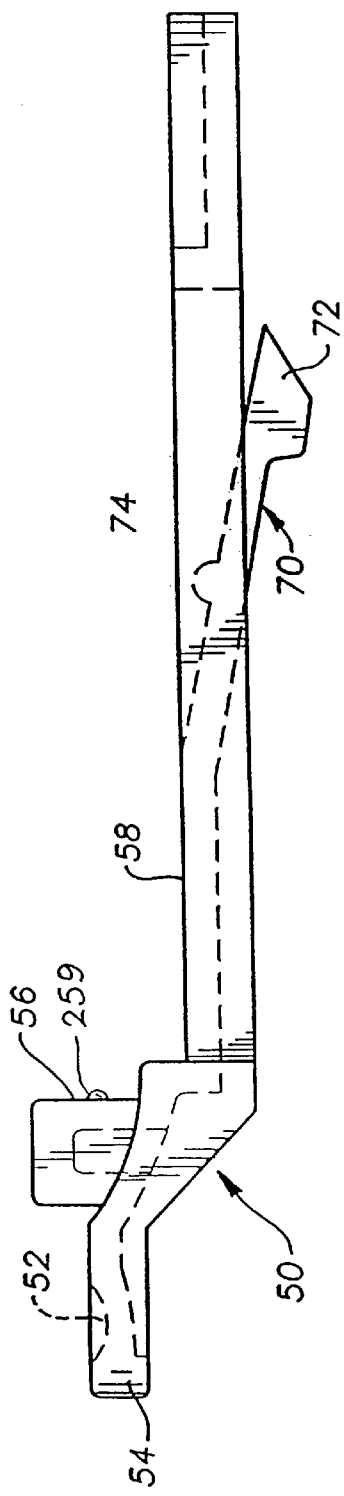
FIG. 3
FIG. 4

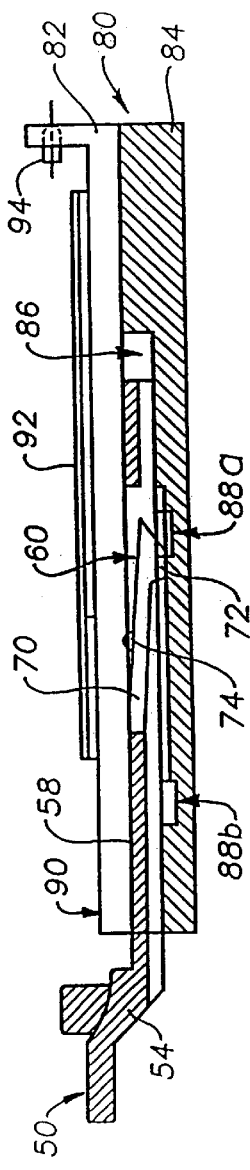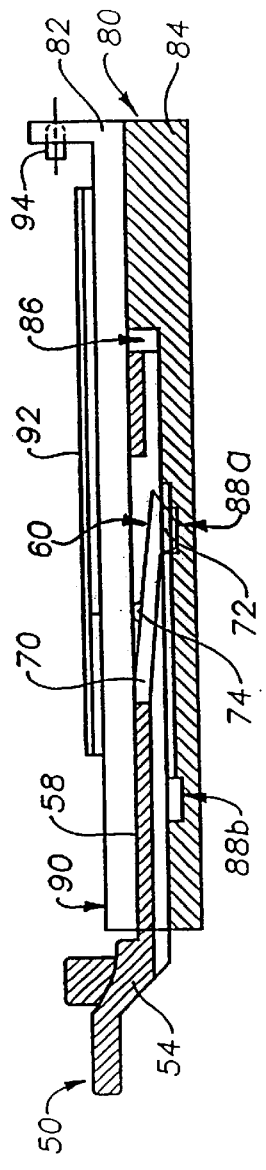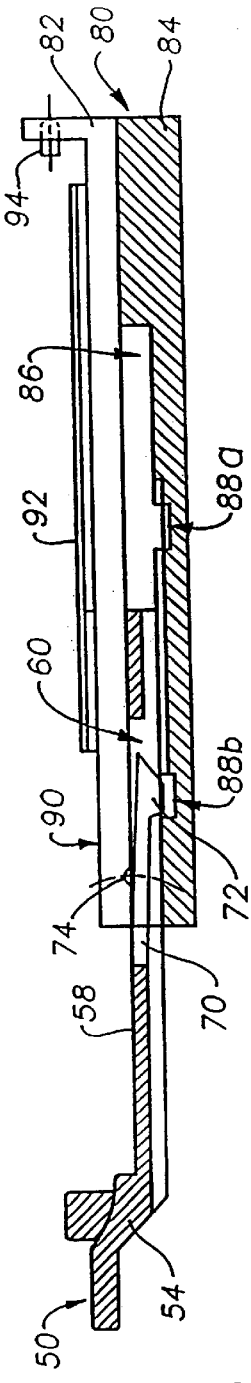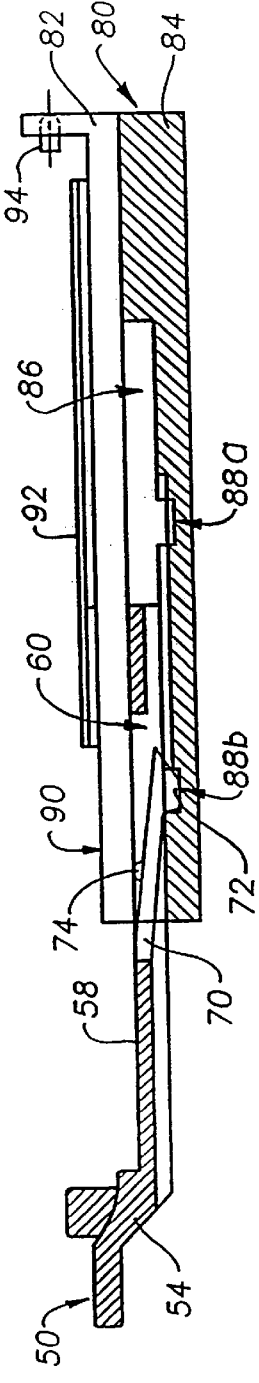

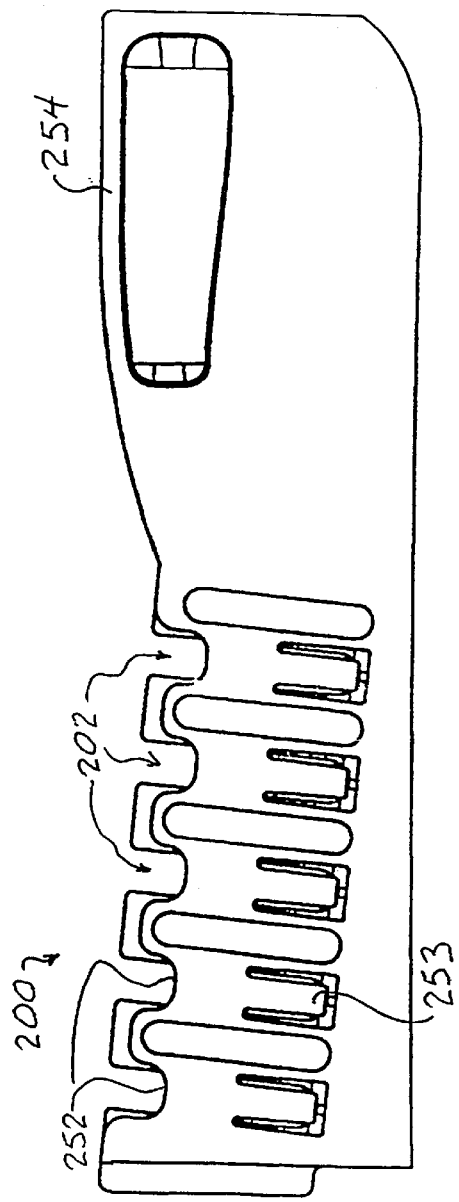
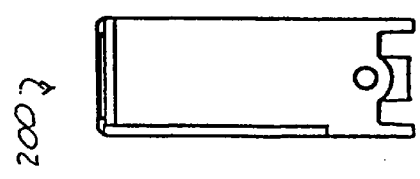
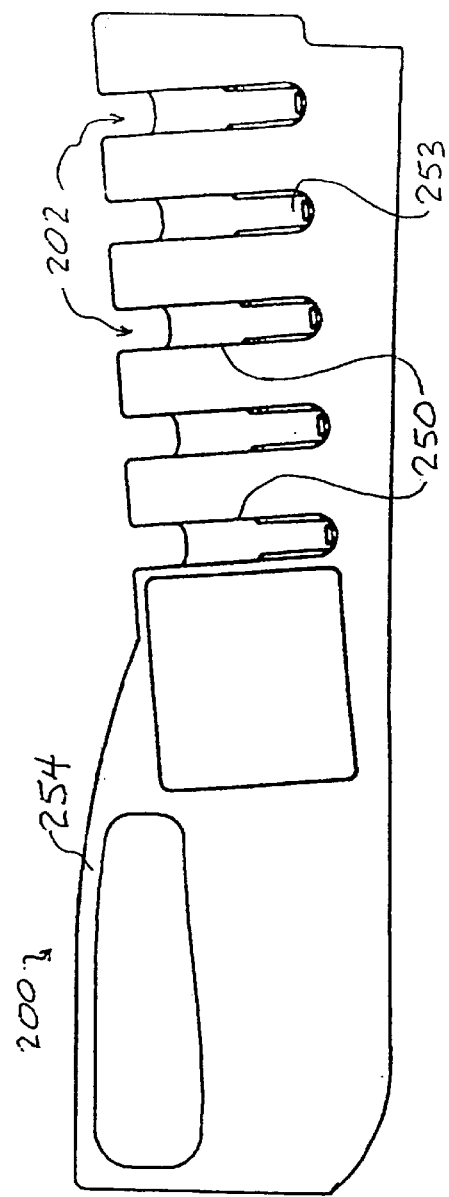
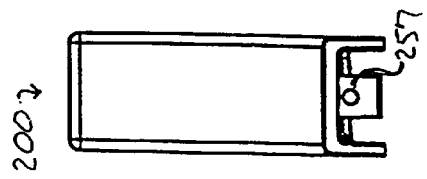

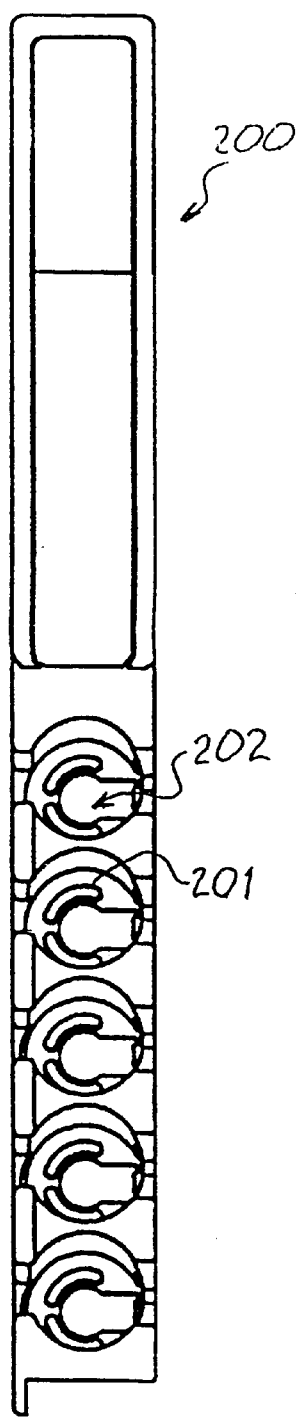
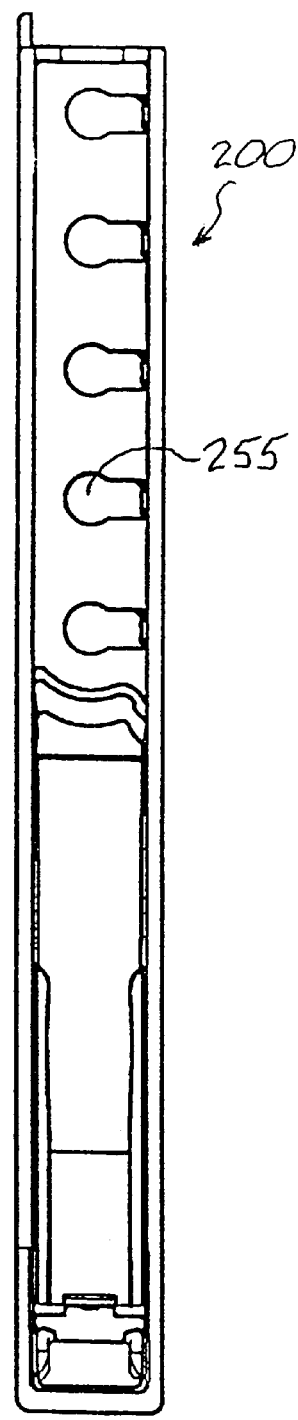
Fig. 30
Fig. 31

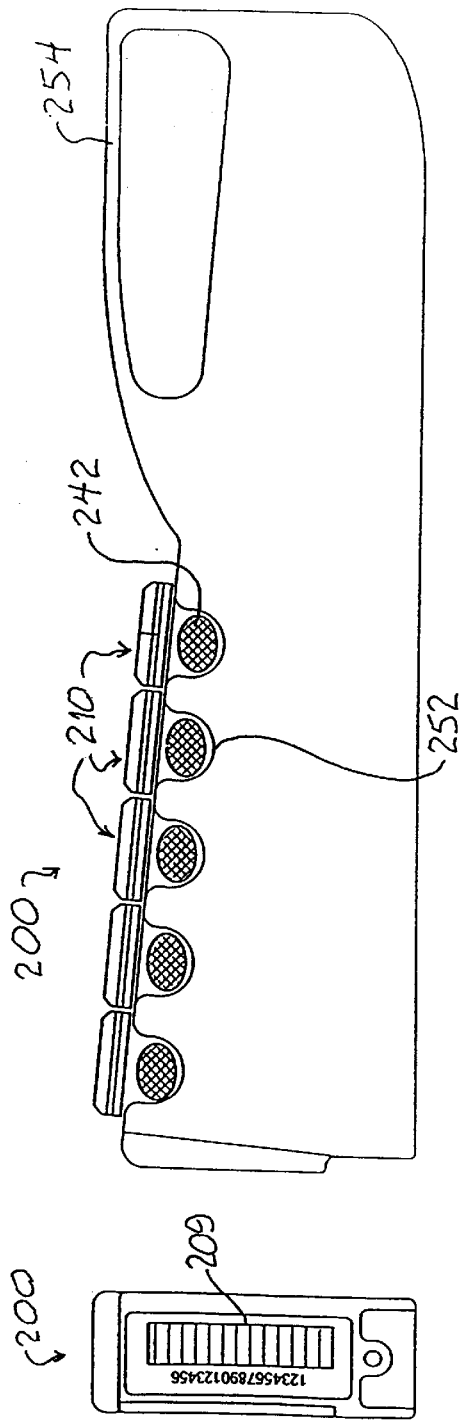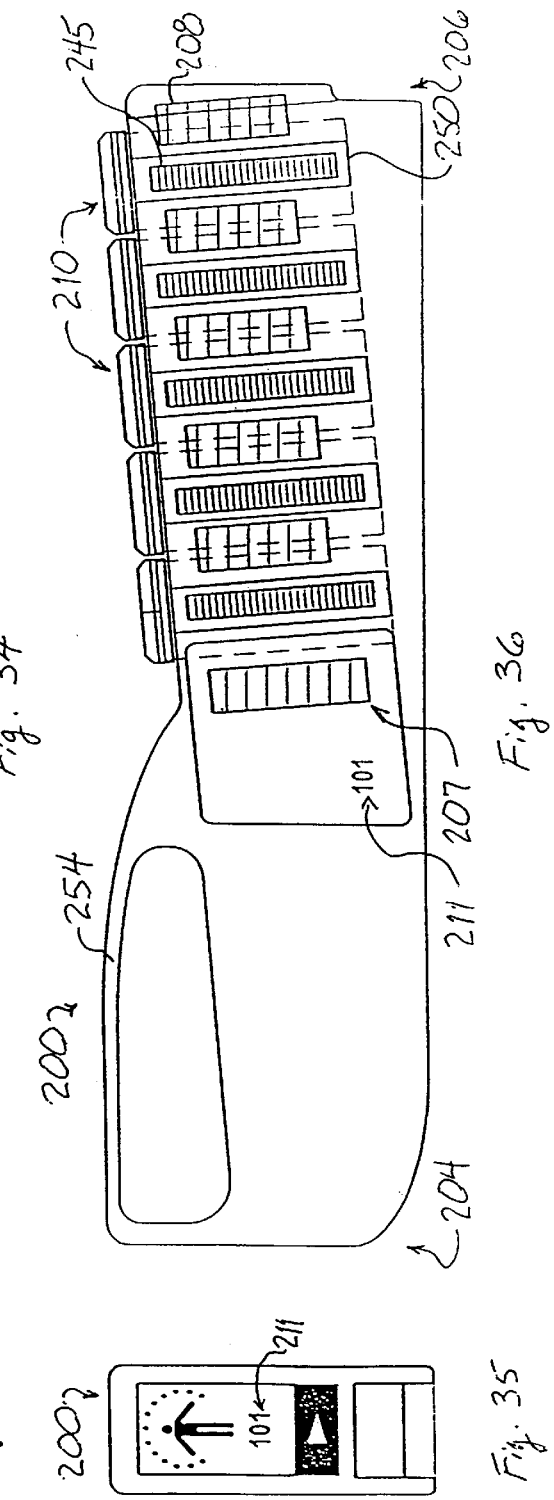

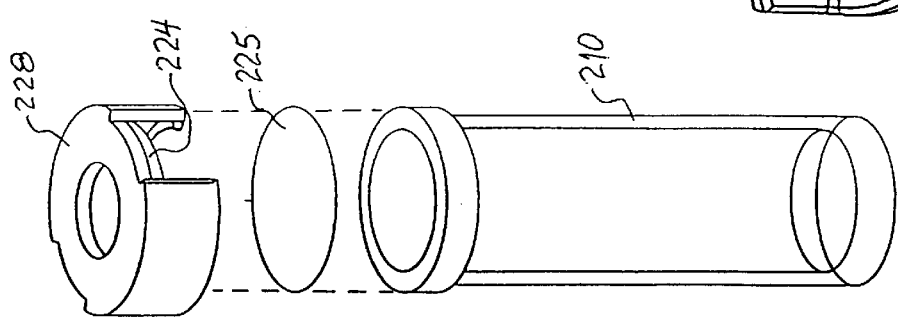
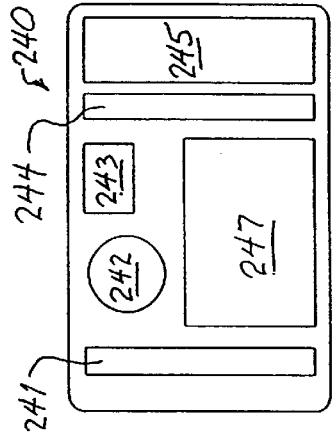
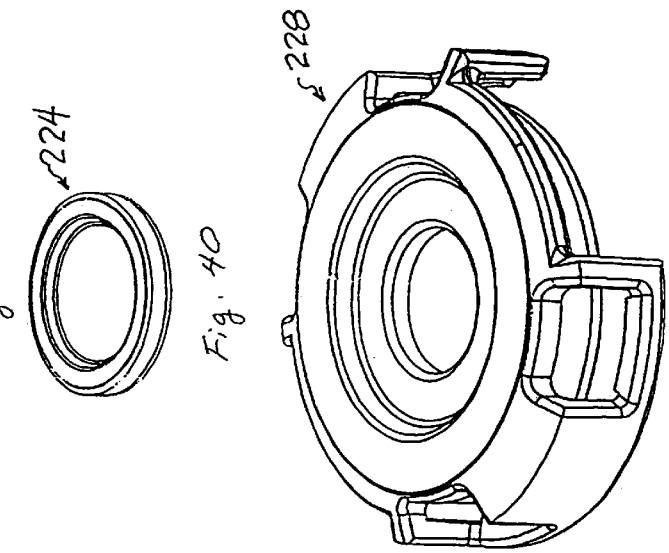
Fig. 44
Fig. 43
Fig. 40
Fig. 41
Fig. 42

REAGENT HANDLING SYSTEM AND CONFIGURABLE VIAL CARRIER FOR USE THEREIN

CROSS REFERENCE TO RELATED APPLICATIONS

This application is a continuation of U.S. patent application Ser. No. 09/099,368 filed on Jun. 18, 1998, now U.S. Pat. No. 6,066,300, which was a continuation in part of U.S. patent application Ser. No. 08/742,014 filed on Oct. 31, 1996, now U.S. Pat. No. 5,788,928, which was a continuation of U.S. patent application Ser. No. 08/499,271 filed on Jul. 7, 1995, now U.S. Pat. No. 5,609,822.

STATEMENT REGARDING FEDERALLY SPONSORED RESEARCH OR DEVELOPMENT

FIELD OF THE INVENTION

The present invention relates to liquid handling systems, and in particular to a configurable allergen handling system.

BACKGROUND OF THE INVENTION

Automated assay devices such as immunoassay instruments provide multiple reagent containers for executing a plurality of individual assays. Storage space for each reagent container has become a significant aspect of instrument design in that more than one reagent is typically required for each assay. Further, the desire to automate dictates that such instruments operate with minimal operator intervention, thus emphasizing the need for adequate quantities of reagent in each container.

Any solid phase reagent, and in particular one including paramagnetic particles, requires physical agitation for uniform suspension in a liquid medium. Further, other materials such as incompatible liquids (e.g. oil and water) require similar agitation for homogenous distribution. Existing means for accomplishing this agitation include axial rotation of cylindrical containers having mixing fins therein. However, such mechanisms are necessarily complex to implement, difficult to maintain, and each require significant physical space. Further, such containers are not accessible during instrument operation. Seals for such containers are typically provided as a "star cap", or resilient cap having star-shaped slits. Such caps provide an insufficient barrier to long-term evaporation and to spillage when the container is tipped.

In general, the most significant requirements for individual reagent containers and for housings holding such containers include the following. Each container should include multiple compartments such that all reagents required for a single assay are accommodated. A sufficient quantity of reagent(s) should be accommodated within each reagent container for unattended execution of a series of tests, such as 50 to 250 assays, or more. The containers should be arranged within the housing for simple removal and installation, even during instrument operation. Evaporation and spillage of reagents stored within the pack should be avoided by provision of improved sealing means. Finally, efficient and mechanically simple solid particle suspension should be implemented, allowing continued mixing during instrument operation.

In addition, certain classes of assays require specific reagents selected from a substantial universe of reagents. For instance, allergy testing in an automated immunoassay instrument requires a significant number of specific allergens chosen from among an even larger number representing all possible allergens. Thus, a need exists for providing an automated assay device with a large number of reagents in various combinations, depending upon the assays to be run, and with information as to where each desired reagent is located for automated aspiration within the device. Given a large number of reagents, it is necessary for the device to have a simple but comprehensive capability for learning how the selected reagents are configured for proper aspiration within the device.

BRIEF SUMMARY OF THE INVENTION

The presently disclosed invention provides all the required reagents for multiple iterations of a single assay within minimal space, yet enables mechanically simple and complete admixture of solid reagents within a carrier. Each reagent pack is fully accessible during instrument operation, provided only that reagents from the desired pack are not currently being aspirated or are about to be so aspirated. A pierceable seal in each of multiple reagent pack lid apertures prevents reagent spillage during pack mishandling, minimizes reagent evaporation, and prolongs reagent efficacy. Pack refrigeration further prolongs reagent efficacy.

The present invention provides a reagent pack having at least one chamber for containing all reagents required for a single assay. In a first embodiment, at least one chamber has offset baffles extending from chamber side walls toward the opposing side wall, providing converging and diverging ductwork. The ductwork forms a narrow throat interconnecting two sub-chambers. Suspended reagent or other reactive material flows through this throat region at an accelerated velocity during reagent pack inclination, resulting in agitation and homogenous reagent suspension within each sub-chamber. A continuous lid, sealable to an upper edge of the pack, provides access to underlying chambers via respective apertures in the lid. The reagent pack is disposed on a reagent enclosure tray, and is urged into and out of the enclosure by a respective slide. Provision is made for disposition of multiple packs in a side by side relationship within the enclosure. Inclination of the packs for proper reagent mixing is provided by a motor which periodically tilts the tray back and forth about a central axis.

The reagent packs are accessible to users once a handling system door is lowered. In this position, a number of optical annunciators each corresponding to a respective reagent pack and slide indicate whether the reagent pack is available for manual removal and perhaps replacement. Tray inclination is inhibited during such access. Efficacy of reagents within the enclosure is prolonged by cooling means such as thermal electric devices and heat sinks disposed proximate the enclosure.

A further aspect of the present invention provides a vial carrier having plural reagent compartments disposed linearly along the length of the carrier. Each compartment is adapted for receiving one of plural reagent vials. The carrier is provided with indicia, such as a bar-code, uniquely identifying it to an automated assay device such as an immunoassay instrument. Similarly, each compartment of the carrier has associated with it indicia which are at least unique to the particular carrier. Lastly, each vial installable within a carrier compartment has indicia unique to the contents of the vial. In a further embodiment, the vial indicia are unique to both the vial contents as well as the capacity of the vial.

Vials in the presently disclosed invention are preferentially provided in plural capacities, depending upon the frequency with which reagent contained therein is likely to be utilized within the automated immunoassay instrument. The vials also preferentially employ an integrated cap/seal assembly to minimize evaporation after initial aspiration from the vial. In a further embodiment, a film seal is applied to the vial opening prior to the cap/seal assembly for the purpose of ensuring that the assembly is liquid-tight during handling, shipping and storage, prior to first use within the automated instrument.

In one embodiment of the present invention, the carrier is configured to be disposed on the reagent enclosure tray described above, and is urged into and out of the enclosure by a respective slide, such as the slides described above with respect to the reagent packs. As with the reagent packs, the presently disclosed carriers may be disposed in side by side relationship within the enclosure of the automated instrument. Tray inclination and environment control are also provided in one embodiment, as previously described.

Data reflecting which specific vial is located in which compartment of a given carrier is collected and provided to the automated instrument prior to installation of the carrier into the enclosure. This can be done directly, for instance through the use of a bar-code scanner associated with the instrument, by sequentially detecting: first compartment indicia, indicia associated with the vial installed in the first compartment, second compartment indicia, indicia associated with the vial installed in the second compartment, etc., until all of the compartments and associated vials have been scanned, then scanning indicia identifying the carrier. Intelligence can also be provided to the instrument such that compartments and respective vials are properly identified regardless of scanning order. Alternatively, this data can be gathered manually and entered into the automated instrument via an interface such as a keyboard or touch sensitive display screen. Once the carrier-specific vial information has been provided to the automated instrument, the carrier is then ready for installation. The automated instrument has, associated with the enclosure, means for recognizing and interpreting the indicia provided on each installed carrier. In this manner, the instrument has information reflecting that a desired vial is installed in a particular compartment of a carrier which is installed on a particular slide within the enclosure.

Enhanced configurability for a system requiring a large subset of individually packaged reagents from among a significant universe of such reagents is thus enabled. At the same time, a high degree of reagent density is provided, enabling the maximization of the number of reagents accessible within an automated immunoassay instrument at any one time.

BRIEF DESCRIPTION OF THE SEVERAL VIEWS OF THE DRAWING

These and other features of the present invention are more fully set forth below in the fully exemplary detailed description and accompanying drawings of which:

FIG. 3 is a perspective view of a reagent pack slide as used in the reagent handling system of FIG. 2;

FIG. 4 is a side view of the slide of FIG. 3 showing internal details in phantom;

FIGS. 5 through 8 are side views of the slide of FIG. 4 installed to varying degrees within a tray of the reagent handling system of FIG. 2;

FIG. 26 is a front view of a vial carrier according to the presently disclosed invention;

FIG. 27 is a right-side view of the vial carrier of FIG. 26;

FIG. 28 is a rear view of the vial carrier of FIG. 26;

FIG. 29 is a left-side view of the vial carrier of FIG. 26;

FIG. 30 is a top view of the vial carrier of FIG. 26;

FIG. 31 is a bottom view of the vial carrier of FIG. 26;

FIG. 33 is a front view of the vial carrier of FIG. 26 having a identifying indicia applied thereto;

FIG. 34 is a right-side view of the vial carrier of FIG. 33;

FIG. 35 is a rear view of the vial carrier of FIG. 33;

FIG. 36 is a left-side view of the vial carrier of FIG. 33;

FIG. 40 illustrates a seal employed in conjunction with the vial of FIG. 37;

FIG. 41 illustrates a cap employed in conjunction with the vial of FIG. 37;

FIG. 42 is an exploded view of a cap, seal, film and vial, all according to the presently disclosed invention;

FIG. 43 is a label for use in conjunction with the vial of FIG. 37;

FIG. 44 illustrates an exemplary display for configuring an analyzer according to the contents of the vial carrier of FIG. 26;

DETAILED DESCRIPTION OF THE INVENTION

Figure 1:
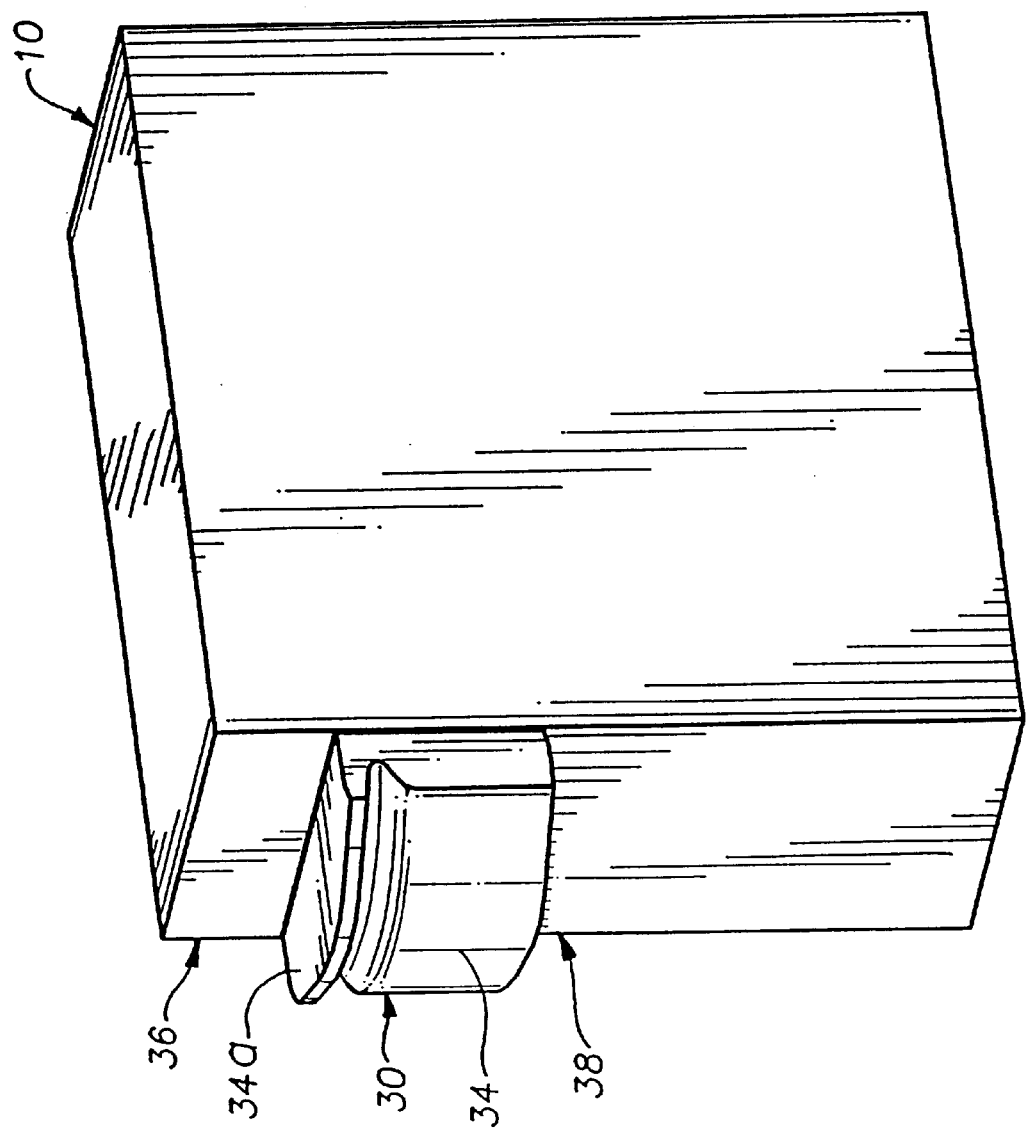
FIG. 1 is a perspective view of an automated analyzer system of which the presently described and claimed reagent handling system forms a part.

Referring now to FIG. 1, an automated analyzer system 10 for performing assays includes a reagent handling system 30 which here is covered by a reagent door 34 having a shelf portion 34a. Located above the reagent handling system 30 is a probe system 36 which aspirates reagents from the reagent system 30 and dispenses the reagents at predetermined locations of the analyzer instrument 10. The analyzer system further includes a refrigeration unit 38 which is provided to cool reagents installed in the analyzer system 10, and in the reagent handling system 30 in particular. The reagent handling system 30 and refrigeration unit 38 will each be described in further detail subsequently.

Figure 2:
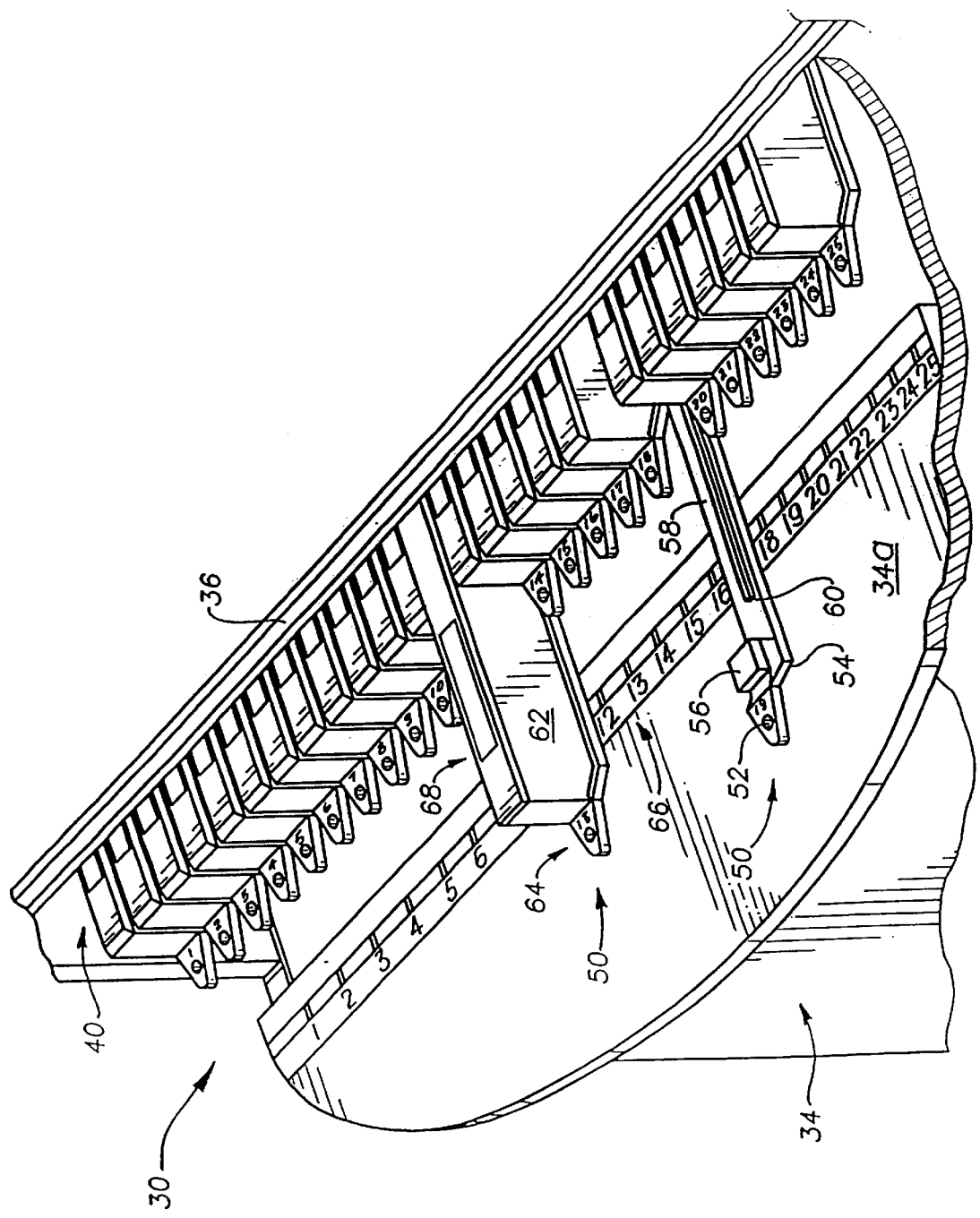
FIG. 2 is a partial perspective view of the reagent handling system as used in the automated analyzer system of FIG. 1.

With regard to FIG. 2, a portion of the reagent handling system 30 is now described. A first embodiment of a reagent door 34, which is shown in an elevated, or closed, position in FIG. 1 is shown in a lowered, or open, position in FIG. 2. Rails (not illustrated) or similar means are employed for maintaining the door 34 in proper alignment with the system 30 in either position. In a second embodiment, the door is hinged at a lower edge thereof. Once the door 34 is opened, multiple reagent packs 62 are seen disposed in a side-by-side relationship proximate respective reagent pack slides 50 within an enclosure generally designated as 40. As will be described further below, the reagent enclosure provides a refrigerated atmosphere which extends the useful life of the reagents or other reactive materials disposed in reagent packs 62 therein. A refrigeration unit 38 (FIG. 1) provides the low temperature atmosphere within the reagent enclosure 40.

Each slide 50, as the name implies, is translatable from an installed position within the reagent handling system 30 and enclosure 40 to a load position in which a portion of the extended slide 50 protrudes over the reagent door shelf 34a. In an illustrative embodiment of the present invention, thirty slides 50 accommodate a like or smaller number of reagent packs 62, each slide being formed of a polycarbonate resin such as Lexan (General Electric Company). The majority of the slides 50 in FIG. 2 are illustrated in the installed position.

With regard also to FIGS. 3 and 4, each slide 50 provides a handle 54 and thumb depression 52 for manually transitioning the slide 50 between the installed and load positions. A reagent pack 62 having a cavity on a bottom surface (discussed subsequently) is disposed proximate a slide upper carrying surface 58 having a post 56, the latter extending into a bottom surface cavity of the reagent pack 62 for maintaining the position of the pack 62 relative to the slide. Each reagent pack 62 is thus safely retained above the respective slide 50 during installation and withdrawal, and during reagent pack inclination, as described below. A retention feature 257 is provided in one embodiment of the slide adapted for receiving a vial carrier, as described subsequently.

In a preferred embodiment, each slide 50 is further provided with a label 64 (FIG. 2) on the slide handle 54 for identifying the relative position of the slide 50 within the row of slides. In the embodiment employing a door 34 which lowers on rails, the slide label 64 corresponds to a numbered optical annunciator 66 such as an LED disposed on the shelf portion 34a of the reagent door 34. When the door 34 is lowered to expose the slides 50 and associated reagent packs 62, illuminated LEDs 66 indicate that the corresponding reagent pack 62 is being accessed by the probe system 36, as described in further detail below, and is therefore prevented from being withdrawn. Once the associated LED 66 is extinguished, this indicates that the reagent pack 62 is not now being accessed or is not about to be accessed by the probe system 36, and is available for withdrawal by pulling the slide 50 outward. In the embodiment employing a door 34 which is hinged at a lower edge, each slide has associated with it two LEDs, one on the door and one on the shelf portion 34a as shown in FIG. 2.

The slides 50 are maintained in side-by-side relationship on a tray, generally designated as 80 in FIGS. 5 through 8. In one embodiment, the tray 80 is provided in at least two parts, a tray upper half 82 and a tray lower half 84. The lower half 84 provides a slot 86 into which the slide extends. In order to maintain the slide 50 in the installed or load positions, or in between, a resilient arm 70 is disposed in a longitudinal slot 60 on the slide 50. This arm 70 has a neutral position which is angled down, for instance, approximately eight degrees from the upper carrying surface 58 of the slide 50.

The bottom surface of the slot 86 has two recesses 88a, 88b. When the slide 50 is fully inserted into the tray 80, an end portion 72 of the slide resilient arm 70 is urged into the forward recess 88a, as illustrated in FIG. 6. The forward recess 88a is relatively shallow, thus allowing the end portion to be removed from the recess 88a as in FIG. 5 by a moderate rearward force, such as exerted by a user pulling the slide 50 out, or to the left as shown.

When a user pulls the slide swiftly to the left, the end portion 72 of the arm 70 is brought into contact with a portion of the lower tray 84 which prevents the removal of the slide 50 entirely without the use of a tool such as a narrow screw driver or fingertip to further elevate the arm 70 and end portion 72. In FIG. 7, the arm 70 has been pushed upward by such a tool so that the end portion 72 is level with an upper surface of the tray lower half 84.

In order to prevent inadvertent withdrawal of the slide 50, the arm 70 is further provided in the illustrated embodiment with a knob 74 which contacts a lower surface of the tray upper half 82 before the arm end portion 72 is elevated enough for slide withdrawal. The effect of the knob 74 pressing against the tray upper half 82 is to shorten the length of the flexible arm 70, thus providing a stiffer arm 70 which offers more resistance to upward motion. In the illustrated embodiment, the knob 74 cuts the arm 70 length roughly in half, thus effectively doubling the arm 70 spring constant.

In a normally withdrawn or extended position, the end portion 72 extends into the rearward recess 88b, as in FIG. 8. Subsequent insertion of the slide into the tray 80 is accomplished by pushing the slide handle 54 to the right, thus causing the end portion 72 to become disengaged from the rearward recess 88b. Over-insertion of the slide 50 is prevented by the proximity of the slide handle 54 to the tray upper half 82 when the slide 50 is fully inserted, shown in FIG. 6.

As shown in FIGS. 5 through 8, the slide 50 is inserted under the tray upper half 82. An upper surface 90 of the tray upper half 82 provides a surface for a reagent pack 62 to slide across as the pack 62 is inserted into the reagent handling system 30. Thus, while the reagent pack 62 is installed over the slide post 56, the reagent pack 62 actually rides on the upper surface 90 of the tray upper half 82. The reagent pack 62 itself will be described in further detail below. However, to improve the efficiency of reagent pack 62 cooling via the tray 80 acting as a cold plate, it is noted that elevated portions 92 of the tray upper half 82 minimize an air gap between a bottom surface of the reagent pack 62 and the tray 80, thus improving thermal conductivity. Further, a retaining pin 94 or similar device is disposed on the tray upper half 82 for engagement with a cooperating reagent pack receptacle (described below), thus ensuring proper alignment of the reagent pack within the tray 80.

The reagent packs 62 visible in FIG. 2 proximate respective slides 50 are now described in greater detail with respect to FIGS. 9 through 12. The reagent packs are formed of high density polyethylene (HDPE) in a first embodiment. Other materials are employable taking into consideration the requirement that the material chosen be non-reactive with the intended pack contents. Cost is another important consideration for pack materials in some embodiments.

Figures 9, 10:
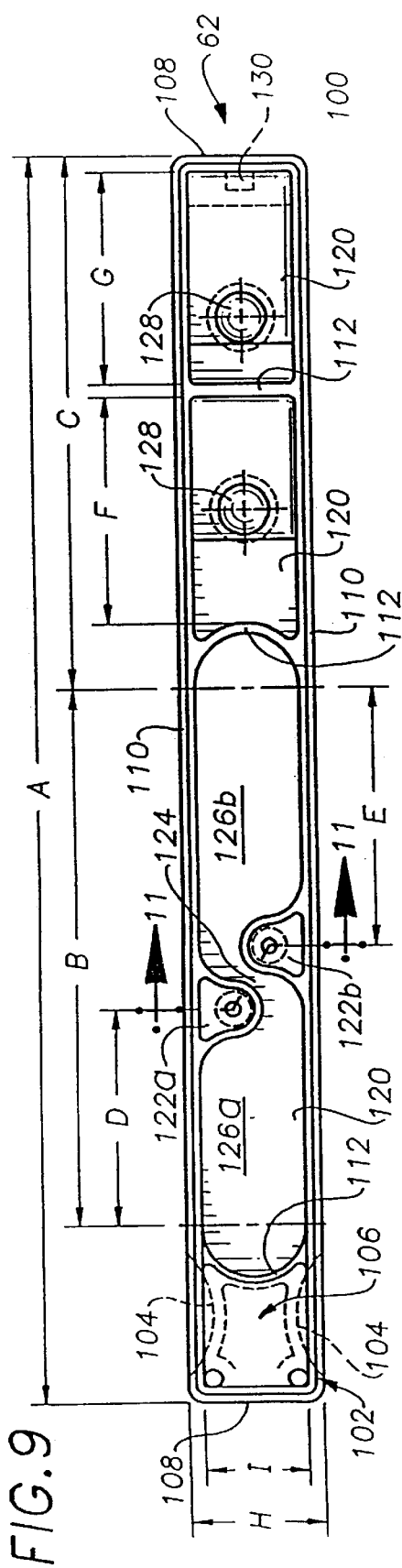
FIG. 9 is a top view of a reagent pack as used in the reagent handling system of FIG. 2.
FIG. 10 is a side sectional view of the reagent pack of FIG. 9.
Figure 11:
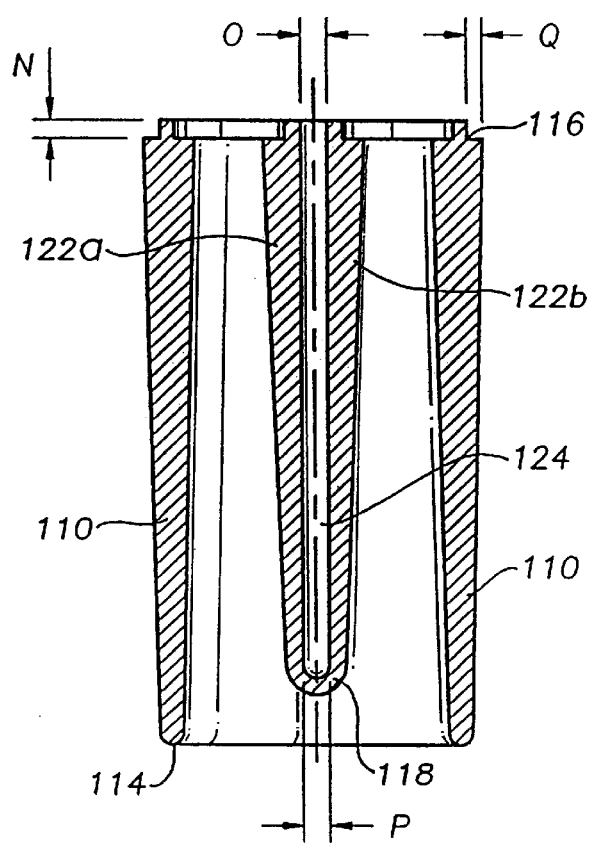
FIG. 11 is a cross-sectional view of the reagent pack of FIG. 9.

FIGS. 9 and 10 illustrate a reagent pack 62 having a forward end 100 and a rearward end 102. In FIG. 2, the forward end 100 is inserted within the reagent handling system 30, and the rearward end 102 is visible proximate the slide handle 54. In a preferred embodiment of the present invention, the rearward end 102 has a pinched region 104 which facilitates manual manipulation of the reagent pack 62. Disposed within the pinched region 104 and disposed within a lower surface thereof is a cavity 106 which receives the slide post 56, thus enabling the slide 50 to usher the reagent pack 62 into and out of the handling system 30.

The reagent pack illustrated in FIGS. 9 and 10 is partially defined by end walls 108, side walls 110, and intermediate walls 112. While the end and side walls 108, 110 extend from a lower edge 114 of the reagent pack 62 to an upper edge 116, not all of the intermediate walls 112 extend down to the lower edge 114. Rather, a floor surface 118 is disposed proximate but slightly above the lower edge 114, and the intermediate walls 112 extend from this surface 118. Together, these walls and surfaces divide each reagent pack interior into a plurality of chambers 120. The floor surface 118 within each of these chambers is canted toward one location, in a first embodiment, in order to facilitate complete withdrawal and usage of material stored therein. In a preferred embodiment, this location takes the form of a depression 128 in the floor surface 118 at a rear portion of each chamber.

Each of the aforementioned chambers 120 are intended for storage of reagents used by the analyzer system 10. In certain cases, the reagent is soluble, and thus requires little or no agitation for homogenous distribution within the chamber 120. Other reagents, however, are not soluble, and do require agitation for continuous distribution throughout the respective chamber 120. As a result, at least one of the chambers of each reagent pack according to the present invention is provided with a pair of opposing, offset baffles 122a, 122b.

These baffles 122a, 122b, each of which extend from a respective side wall 110 toward the opposite side wall 110, are vertically disposed from the floor surface 118 to the upper edge 116 of the side wall 110, and preferably extend across at least half the width of the reagent pack 62 toward the opposing side wall 110. Further, while one of the baffles 122a is disposed closer to the reagent pack rearward end 102 than the other baffle 122b, they are close enough to one another to form a ductwork having converging then diverging walls, otherwise referred to as a narrow throat 124 within the respective chamber 120. The baffles are illustrated in the composite sectional view of FIG. 11, and while being omitted from the side sectional view of FIG. 10 for clarity.

In an alternative embodiment which is not illustrated, the baffles 122a, 122b do not extend all the way up to the upper edge 116 of the side wall 110. Instead, the baffles terminate proximate the upper edge 116, and slope downward as they extend across the width of the reagent pack. This embodiment is particularly useful for reagents which foam when agitated, since it allows the foam to pass back and forth unhindered as the reagent pack is tilted. Otherwise, the foam would have a tendency to impede the flow of reagent through the ductwork, limiting the effectiveness of the agitation. In fact, the free movement of the foam above the baffles provides a further benefit in that it tends to promote the dissipation of the foam.

Figure 12:
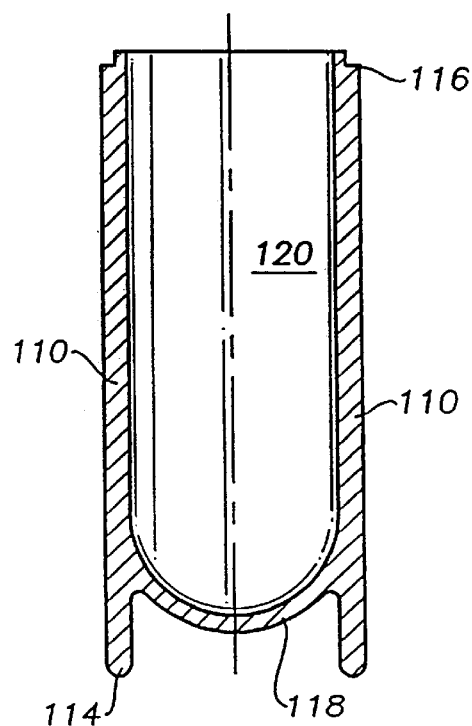
FIG. 12 is a cross-sectional view of the reagent pack of FIG. 9.

In particular, the larger chamber 120 in FIG. 9 and shown in representative cross-section in FIG. 12 is shown divided into two sub-chambers 126a, 126b of substantially equal volumes, each of the sub-chambers 126a, 126b interconnected by the throat 124. The benefit of such a configuration is realized when suspended reagent materials are introduced into this divided chamber 112, and the reagent pack 62 is tilted back and forth about an axis under the reagent pack and orthogonal to the slide 50. Fluent material, carrying the suspended reagent, greatly accelerates as it passes through the throat 124, resulting in significant agitation of the reagent and fluent carrier through currents circulating about the perimeter of the sub-chambers. Complete, homogenous distribution is achieved rapidly, with the exact speed of mixing depending upon the angle of tilt, the frequency of oscillation, the reagent intermixed, the fluent carrier, and the reagent temperature. Means for tilting the tray 80 and the reagent pack 62 disposed thereon are described in detail below.

As previously noted, the reagent pack 62 is installed over a respective slide 50, including a slide post 56, but the reagent pack weight is principally borne by the tray upper half upper surface 90, the lower edge 114 of the pack 62 gliding thereon. The slide is therefore used primarily to impart relocating force to the reagent pack 62 and to retain the reagent pack 62 in the desired position within the handling system 30. Also as previously noted, the tray upper half 82 has a retaining pin 94 (FIGS. 5 through 8) which is received within a reagent pack receptacle 130 (FIGS. 9 and 10) formed proximate the lower edge 114 of the end wall 108 at the forward end 100 of the reagent pack 62. This arrangement ensures the proper alignment of the reagent pack 62 to the remainder of the handling system 30.

Exemplary dimensions for the illustrated reagent pack and for alternative embodiments are provided in table 1. Other reagent pack embodiments have further variations on the illustrated dimensions. All measurements are provided in inch units.

TABLE 1

| DIMENSION | EMBODIMENT 1 | EMBODIMENT 2 | EMBODIMENT 3 |
| --- | --- | --- | --- |
| A | 6.69 | 6.69 | 6.69 |
| B | 3.00 | 2.40 | 3.00 |
| C | 2.83 | 3.13 | 2.83 |
| D | 1.32 | 0.89 | 1.32 |
| E | 1.32 | 0.89 | 1.32 |
| F | 1.15 | 1.15 | 1.15 |

TABLE 1-continued

| DIMENSION | EMBODIMENT 1 | EMBODIMENT 2 | EMBODIMENT 3 |
|---|---|---|---|
| G | 1.20 | 1.20 | 1.20 |
| H | 0.72 | 1.320 | 0.72 |
| I | 0.60 | 1.20 | 0.60 |
| J | 1.895 | 1.895 | 1.895 |
| K | 0.89 | 0.89 | 0.89 |
| L | 1.665 | 1.665 | 0.83 |
| M | 1.449 | 1.449 | 0.600 |
| N | 0.060 | 0.060 | 0.060 |
| O | 0.082 | 0.113 | 0.082 |
| P | 0.072 | 0.103 | 0.072 |
| Q | 0.030 | 0.030 | 0.030 |

Note that in Embodiment 2, the reagent pack is over twice as wide (dimension H) as that of Embodiment 1, thus requiring two adjacent slides 50 for insertion and removal. This embodiment obviously provides a greater quantity of reagent or other reactive material, and thus enables execution of a greater number of assays before pack 62 replacement.

An illustrative embodiment of a reagent pack according to the present invention is illustrated in FIGS. 19 through 25.

Figure 13:
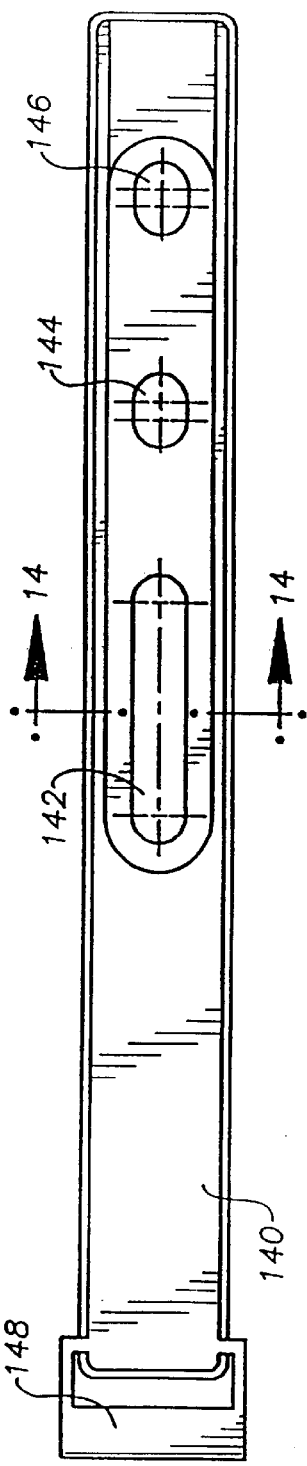
FIG. 13 is a top view of a reagent pack lid as used in the reagent handling system of FIG. 2.
Figure 14:
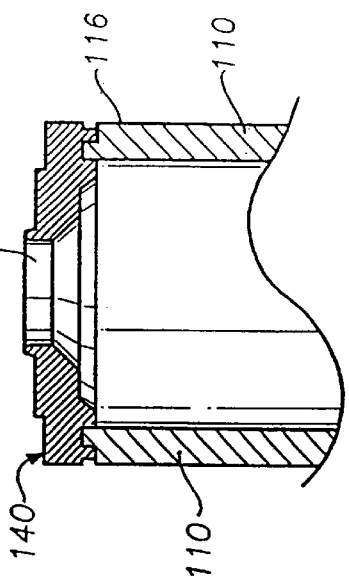
FIG. 14 is a partial cross-sectional view of the lid of FIG. 13 disposed atop the reagent pack of FIG. 9.
Figure 15:
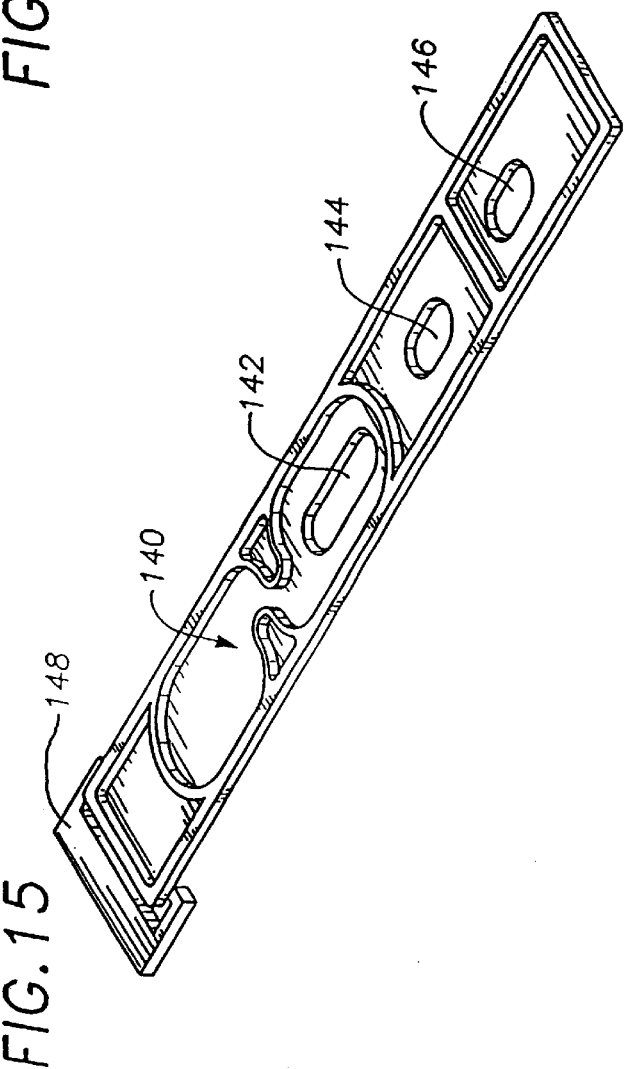
FIG. 15 is a bottom perspective view of the lid of FIG. 13.

In FIGS. 13 through 15, a lid 140 for a reagent pack is illustrated. The lid 140, formed of HDPE in a first embodiment, includes plural apertures 142, 144, 146. Each aperture 142, 144, 146 is covered with a penetrable material such as a combination of polyester and ethyl vinyl acetate (EVA) films in one embodiment, or a combination of polyester and HDPE films in another. Alternatively, a single layer of film is employed. In all embodiments, an important criteria is that the aperture covering material be inactive with the enclosed reagent. The apertures 142, 144, 146 are substantially aligned with respective underlying chambers 120, and preferably with reagent pack chamber floor depressions 128. A needle-like probe, part of the probe system 36, passes through the aperture by penetrating the covering material and extends into a quantity of material such as reagent contained therein for aspiration and use elsewhere in the system 10. The lid 140 is welded hot plate welded onto the upper edge 116 of the reagent pack 62 aperture in one embodiment. In another embodiment, the lid 140 is welded by a non-contact method, as known in the art. The aperture covering material significantly reduces leakage or spillage which result from improper manipulation of the reagent pack.

In a preferred embodiment, the lid 140 is attached to an empty reagent pack 62 shell as previously described. The reagent pack 62 is filled, after which the aperture covering material is applied. Each aperture may be covered separately, or all my be covered by a continuous portion of aperture covering material at once. The reagent pack lid 140 further comprises, in the embodiment illustrated in FIGS. 13 and 15, a tab 148 useful during pack 62 assembly. The tab 148 provides a convenient hand hold when the lid 140 is positioned for attachment to the pack 62. Other embodiments for the tab 148 are possible. After assembly, the tab 148 is removable. Further, the tab 148 may be omitted entirely in another embodiment of the lid 140.

Figure 16:
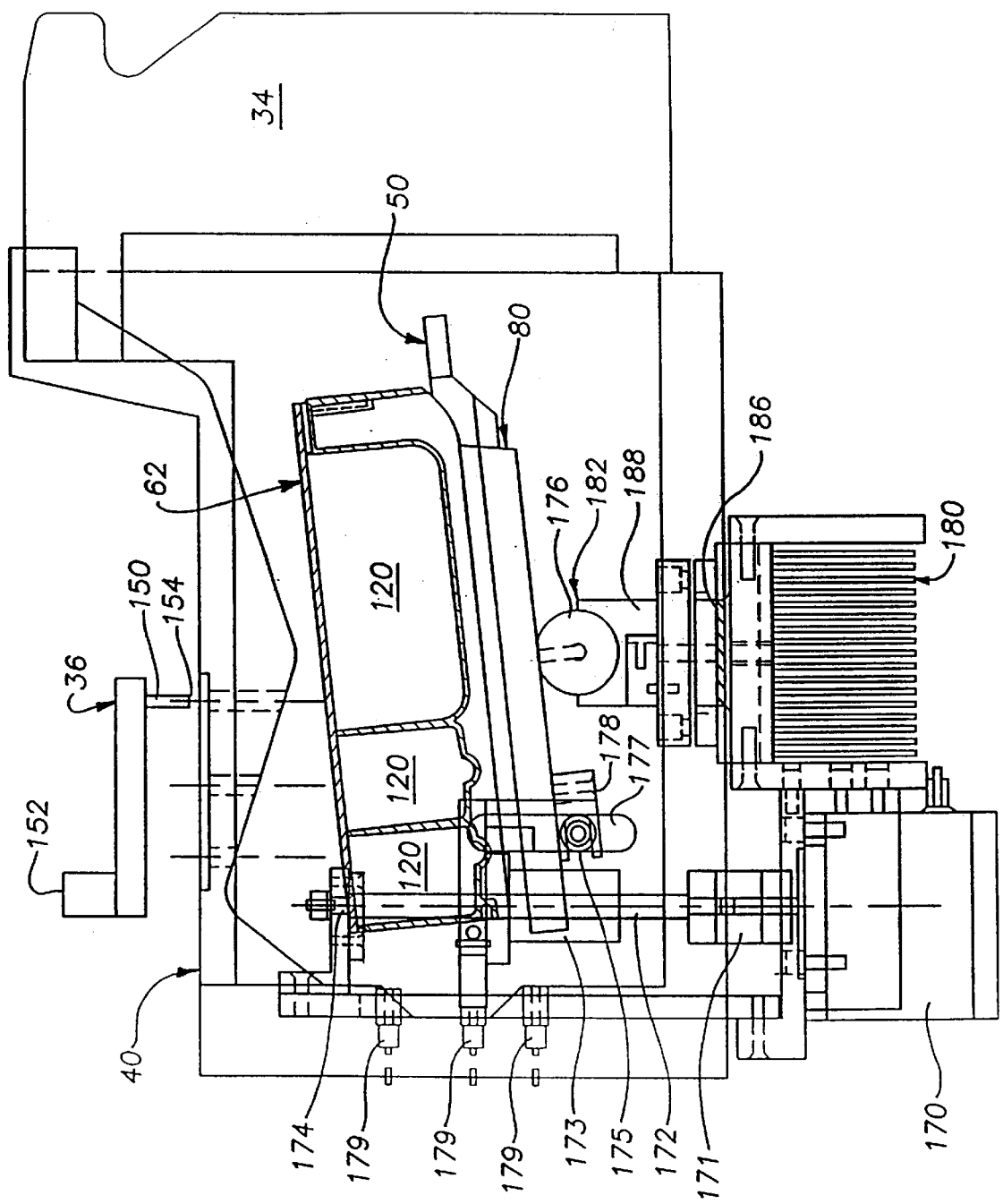
FIG. 16 is an end view of a reagent pack enclosure as used in the reagent handling system of FIG. 2.

The general placement of the probe system 36 with respect to the enclosure 40 is illustrated in FIG. 16, and includes a motor 152 for translating at least one probe tip 154 across and above the reagent packs 62 disposed on the tray 80 in a direction of motion orthogonal to the direction of motion of the slides 50. Further motive means are provided in the probe system 36 for translating the probe tip 154 along the length of a given reagent pack 62. Thus, the probe tip 154 is capable of being positioned above any of the lid apertures 142, 144, 146 and associated chambers 120. A third motive means associated with the probe system 36 controls the vertical position of the probe tip 154. In one embodiment of the present invention, each motive means is provided in the form of one or more stepper motors. In another embodiment of the present invention, three probes 150 are provided within the probe system 36, thus enabling coincidental aspiration between the probes 150.

In another embodiment of the present invention, a bar code label (not illustrated) is disposed on the forward end 100 of the each reagent pack 62 to provide information about the contents of the pack 62 such as type of reagent, quantity, concentration, expiration date, etc. This information is scanned by a bar code reader (not illustrated) disposed within the analyzer system 10 and translated by motive means such as a stepper motor.

In alternative embodiments of the present invention, other means for passing information from a reagent pack to the analyzer system 10 are envisaged. For instance, relevant information may be magnetically encoded in a stripe on the forward end 100 of a reagent pack 62. A magnetic stripe reader would then be employed by the system 10. Further, other optical data transfer techniques are employable, such as optical character recognition.

As previously noted, each reagent pack 62 is disposed above a respective slide 50 and on a portion of a tray 80 within the enclosure 40. In order to preserve the efficacy of reagents or other reactive materials disposed within the reagent packs 62, it is preferred that the enclosure 80 be insulated and refrigerated, with the tray 80 preferably provided in Teflon-coated aluminum to act as a cold plate. Thermo-electric devices (TEDs) 186 (four in one embodiment, and six in another) are disposed proximate to and in thermal communication with an inclination pin 176 through a thermally conductive bearing surface block 188. Together, the inclination pin 176 and the bearing surface block 188 form a thermally conductive hinge 182. Thus, the reagent packs 62 can be inclined about this hinge, the hinge being capable of conducting heat through the bearing surface block 188 to the TEDs 186. Such cold plate cooling is more efficient than air cooling, the latter suffering from loss of cooling effect when the door 34a is opened. In an alternative embodiment, a heat exchanger with a forced convection fan or fans is provided inside the enclosure 40. This latter embodiment preferably further comprises an interrupter switch associated with the door 34 such that the fan(s) is stopped when the door is opened.

In an exemplary embodiment, a thermistor (not shown) associated with each TED 186 is installed within the enclosure 40 for providing a TED control circuit with feedback regarding the current thermal state of the enclosure 40. In an alternative embodiment, there is one such thermistor for every two TEDs 186. The TEDs 186 are further provided with heat sinks 180 below the enclosure 40 in order to enhance the effectiveness of the TEDs. A fan (not illustrated) is provided proximate the fixed heat sink 180 in a further embodiment to further enhance the efficiency of the TEDs 186.

The tray 80, on which the reagent packs 62 rest and in which the slides 50 are disposed, provides support for the packs 62 within the refrigerated reagent enclosure 40. As previously described, the reagent packs 62 are preferably provided with a unique set of mixing baffles 122 which cause turbulence within at least one of the reagent pack chambers 120 when the pack 62 is tilted along its length.

Thus, it is desired that the reagent tray be capable of inclination about an axis orthogonal to the direction of motion of the slides 50 and parallel to the axis along which the multiple reagent packs 62 are disposed within the reagent tray enclosure 40.

Also visible in FIG. 16 is an inclination motor 170 disposed, depending upon the embodiment, at either end or in the middle of the enclosure 40 for providing the power required to incline the tray 80. Preferably, the inclination motor 170 is a stepper motor. Extending axially from the inclination motor 170 is a screw shaft 172 mounted in bearings 174 at the top end of the shaft 172 and coupled to the motor via a coupling 171. Rotation of the shaft 172 causes a follower nut 173 to travel up or down the screw shaft 172, depending upon the direction of rotation. A rocker shaft 175 is affixed to the follower nut 173, is disposed along the length of the enclosure and is mechanically affixed under the tray 80 by a slide block 178. When the follower nut 173 is driven up or down by rotation of the screw shaft 172, the rocker shaft 175 similarly travels up or down in a support bracket channel 177, resulting in the inclination of the tray 80 and associated reagent packs 62 about the pivot shaft 176 which extends parallel to the rocker shaft 175. In a preferred embodiment, the limits of tray 80 inclination are twenty degrees above and below horizontal, though other angular limits are possible depending upon the enclosure space and mixing requirements. Sensors 179 are provided for detecting the angle of inclination.

Figure 17:
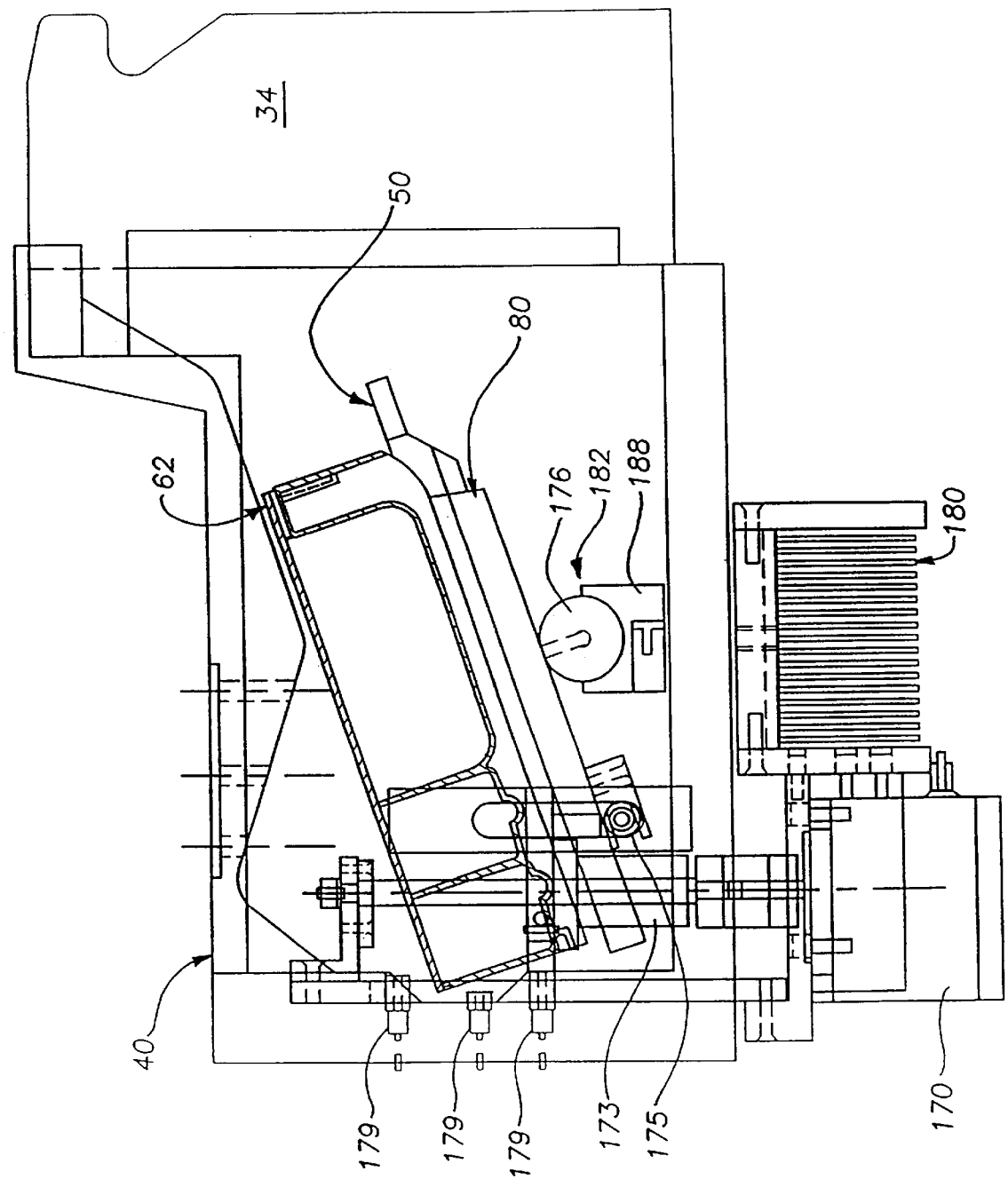
FIG. 17 is a simplified end view of the enclosure of FIG. 16 in a first position.
Figure 18:
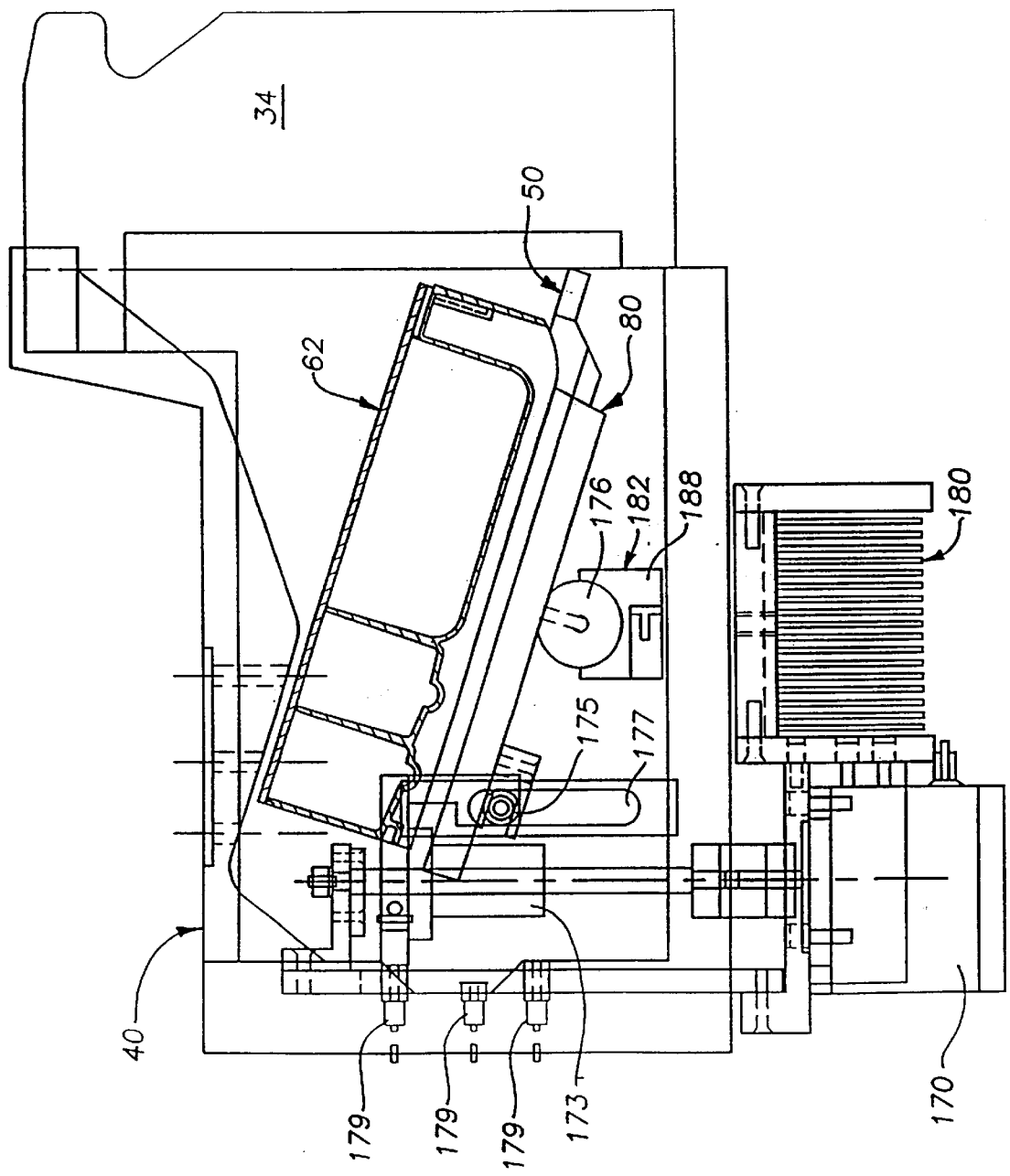
FIG. 18 is a simplified end view of the enclosure of FIG. 16 in a second position.
Figure 19:
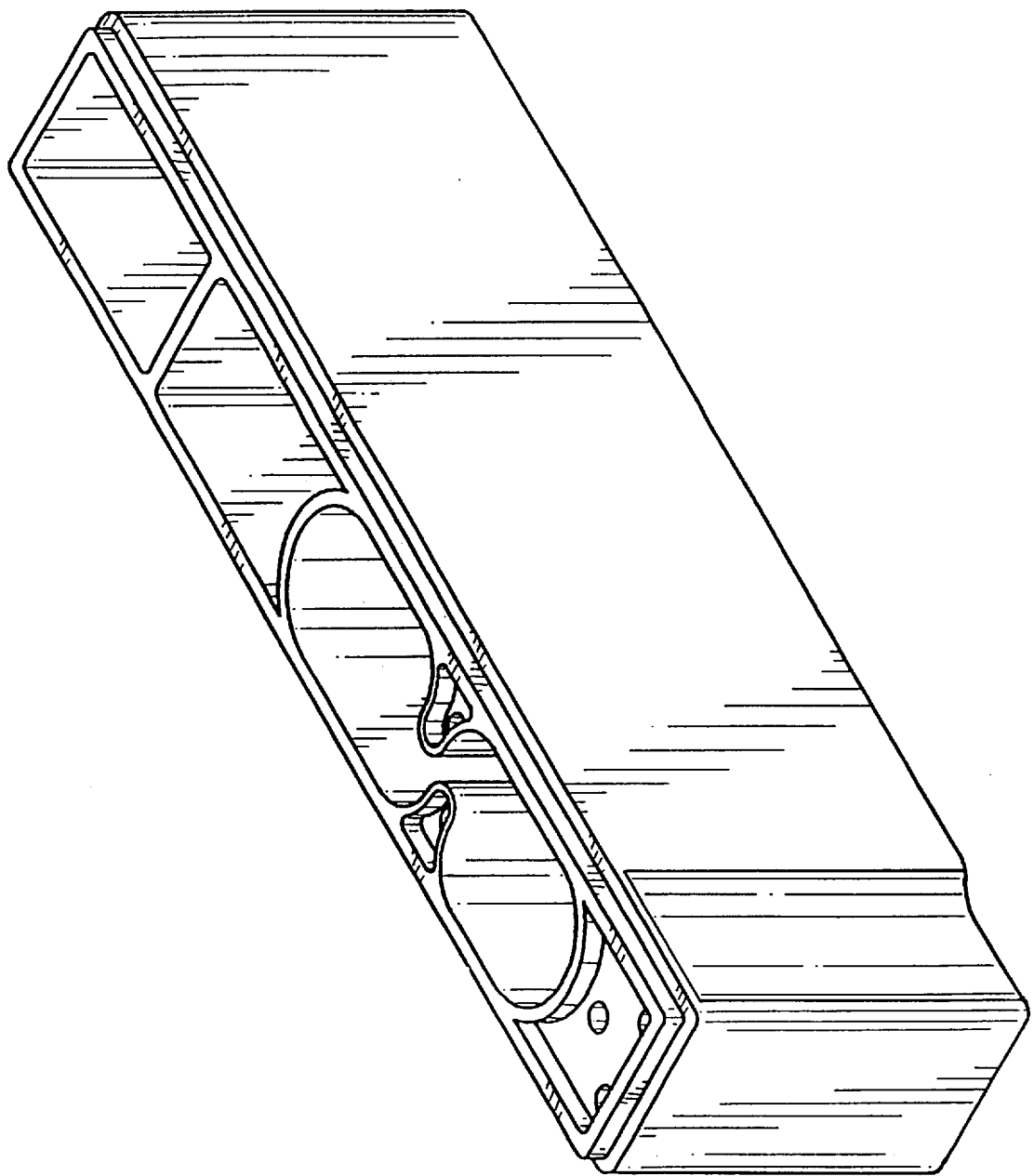
FIG. 19 is a top-right-front perspective view of a reagent pack as used in the reagent handling system of FIG. 2.
Figure 21:
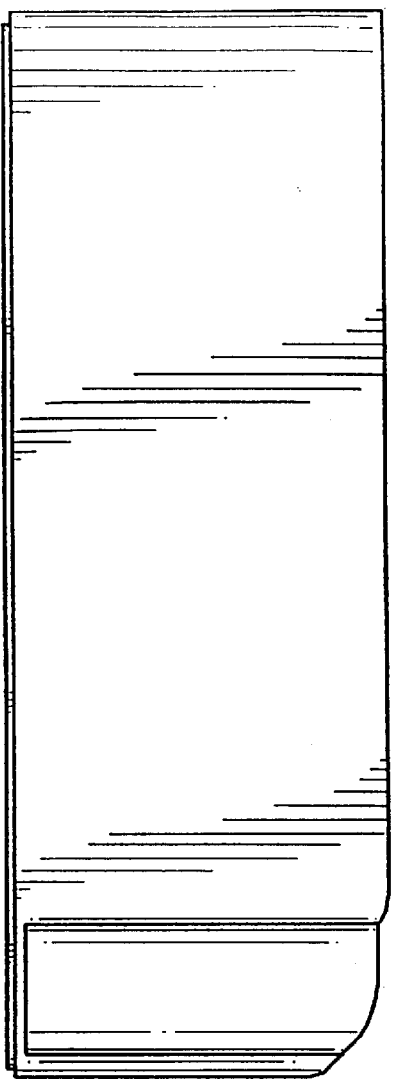
FIG. 21 is a right side view of the reagent pack of FIG. 19.
Figure 23:
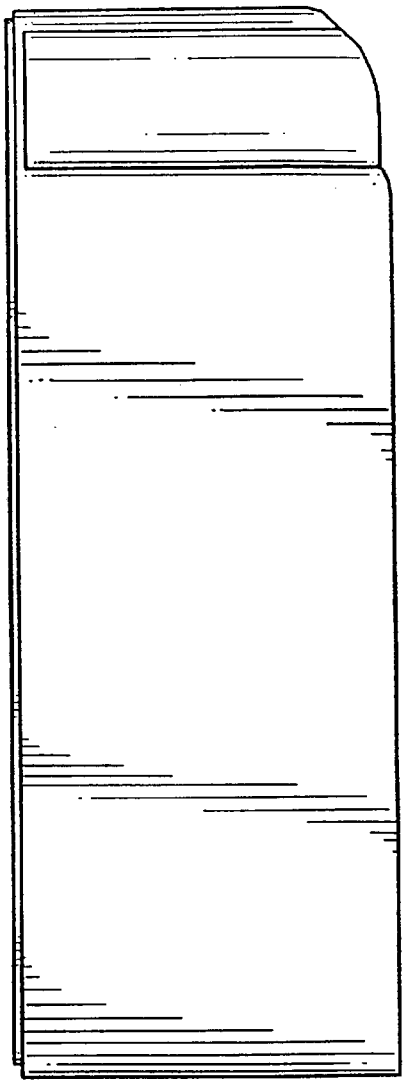
FIG. 23 is a left side view of the reagent pack of FIG. 19.
Figure 20:
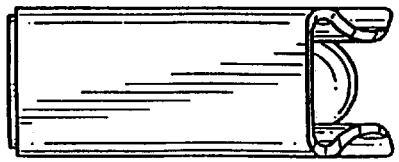
FIG. 20 is a front end view of the reagent pack of FIG. 19.
Figure 22:
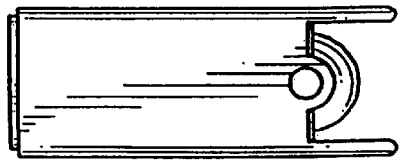
FIG. 22 is a rear end view of the reagent pack of FIG. 19.
Figure 24:
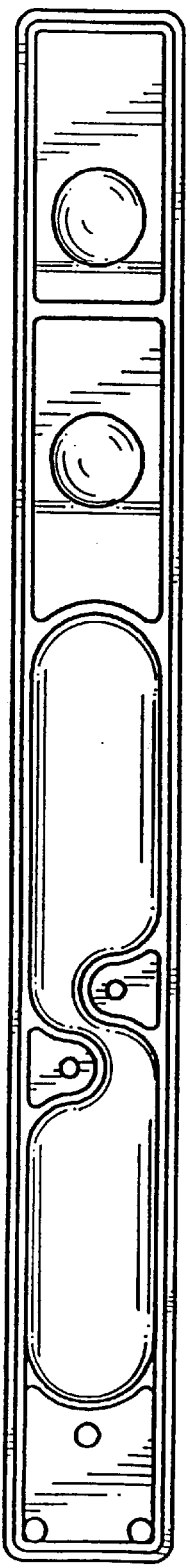
FIG. 24 is a top view of the reagent pack of FIG. 19.
Figure 25:
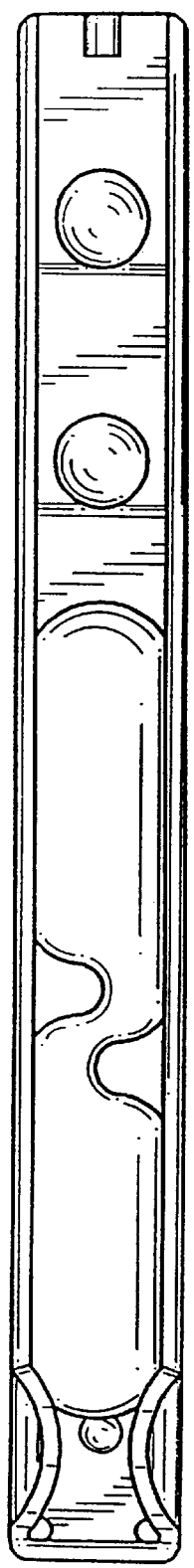
FIG. 25 is a bottom view of the reagent pack of FIG. 19.
Figure 32:
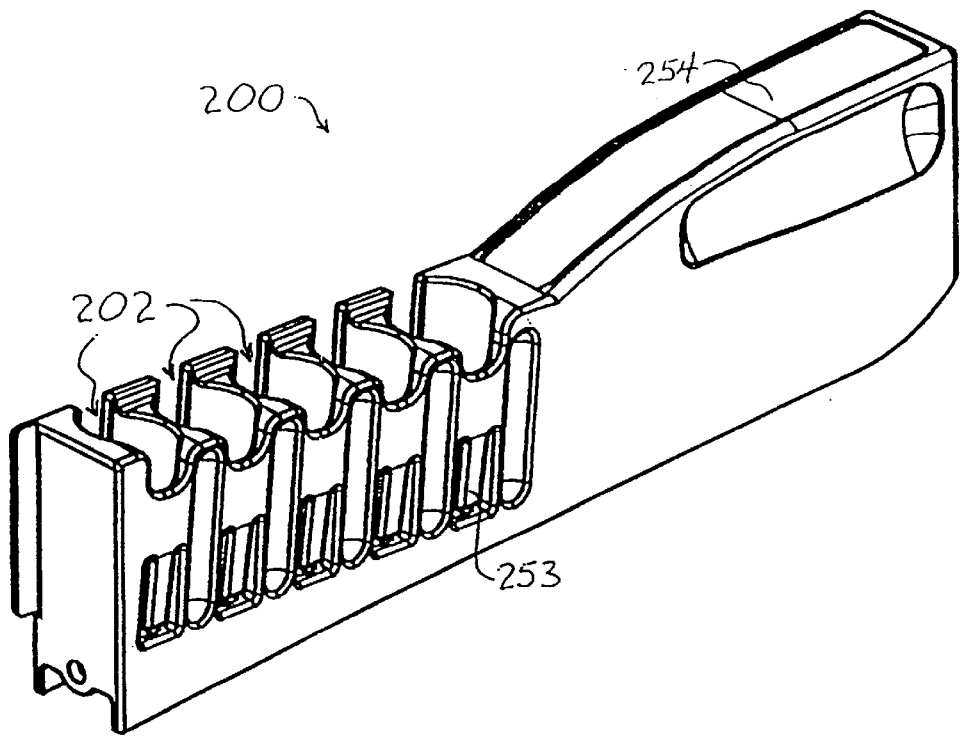
FIG. 32 is a perspective view of the vial carrier of FIG. 26.

In a preferred embodiment of the present invention, the tray 80 is inclined to its twenty degree limits only when the door 34 of the reagent handling system 30 is in the elevated or closed position. Otherwise, the tray 80 is inclined five degrees from horizontal such that the reagent pack forward end 100 is below the reagent pack rearward end 102. As illustrated in the simplified views of FIGS. 17 and 18, with the door 34 in the closed position, the angle of inclination of the front of the tray 80, the end of the tray which receives the slide 50 and reagent pack 62, varies from +20 degrees (FIG. 17) to −20 degrees (FIG. 18), relative to horizontal. Other angular offsets are possible in alternative embodiments. The sensors 179 provide an indication of when the tray 80 is at the limits of inclination.

When the door 34 is opened, depending upon the door embodiment, exposing the reagent packs 62 in the enclosure 40, the inclination motor 170 angles the front of the tray to +5 degrees above horizontal, referred to as an aspirate position, to facilitate removal and installation of reagent packs 62. This angle is illustrated in FIG. 16. Specifically, by locating depressions 128 in the pack floor surface 118 proximate the rear of each chamber, and by canting the floor 118 toward each such depression 128, complete aspiration of reagent contained within each chamber is achieved.

As shown in FIG. 2, a slide 50, disposed on the tray 80 in the aspirate position, is pulled out of the enclosure 40 to provide access to the reagent pack 62 stored thereon. As previously noted, the resilient arm 70 of the slide 50 is retained within tray lower half slot recesses 88a, 88b, maintaining the slide in either of the positions illustrated in FIG. 2.

In one embodiment of the present invention, the tray 80 and associated reagent packs 62 are cycled between the extreme inclination limits five times for approximately six seconds, then are maintained at the aspirate position for nine seconds. Other rates of inclination are possible. Such agitation, combined with the provision of mixing baffles 122 in at least one of the reagent pack chambers 120, allows the present system reagent handling system 30 to accept a reagent pack having a settled solid phase reagent in one chamber 120 and to provide such the solid phase reagent in fully suspended form by the time an assay requires the reagent.

It is while in the aspirate position of FIG. 16 that the plural reagent probes 150 access the underlying reagents through the lid apertures 142, 144, 146. As previously noted, when a reagent pack 62 is being accessed by a probe 150, an associated optical annunciator 66 is illuminated to indicate that the pack 62 should not be removed.

The automated analyzer system 10 of the present invention is also employed to carry out testing which requires a greater number of reagents than can otherwise be provided in the reagent packs 62 previously described. For instance, if the analyzer system 10 is employed to carry out allergy testing, a large number of allergens or mixes of allergens may be required to perform comprehensive testing. Thus, the pre-filled, higher-volume reagent packs 62 previously described may not be appropriate for testing which involves a large number of reagents, carried out in various combinations.

Instead, a vial carrier 200 as shown in FIGS. 26–32 is employed. This carrier 200 provides a plurality of vial compartments 202, configured linearly along the length of the carrier 200. In the illustrated embodiment, five such compartments 202 are employed, though other embodiments employ more or less compartments. By carrying up to five vials in this illustrated embodiment, the carrier 200 enables the use of a greater number of reagents or reagent combinations than that afforded by the reagent pack 62. This is of particular importance if the reagents employed are allergens used for allergy testing.

As shown in FIGS. 27, 29, 34 and 36, each carrier 200 is preferably provided with an integrally formed handle 254 for ease of transport by a user. In one embodiment, when the carrier is placed on a horizontal surface, the vial carrier compartments 202 are angled approximately five degrees from vertical to account for the five degree tilt in the reagent enclosure tray 80 when the tray is in its neutral, or loading/unloading, position, such as in FIG. 16.

Each carrier is preferably as wide as the reagent pack illustrated in FIGS. 9 through 15, such that one carrier 200 is manipulated by a single slide 50. As with the reagent pack 62, the carrier is moved into and out of the enclosure 40, though the carrier is actually resting atop the tray 80 when installed in the enclosure to enhance the effect of the cold plate cooling previously described.

Figures 37, 38, 39:
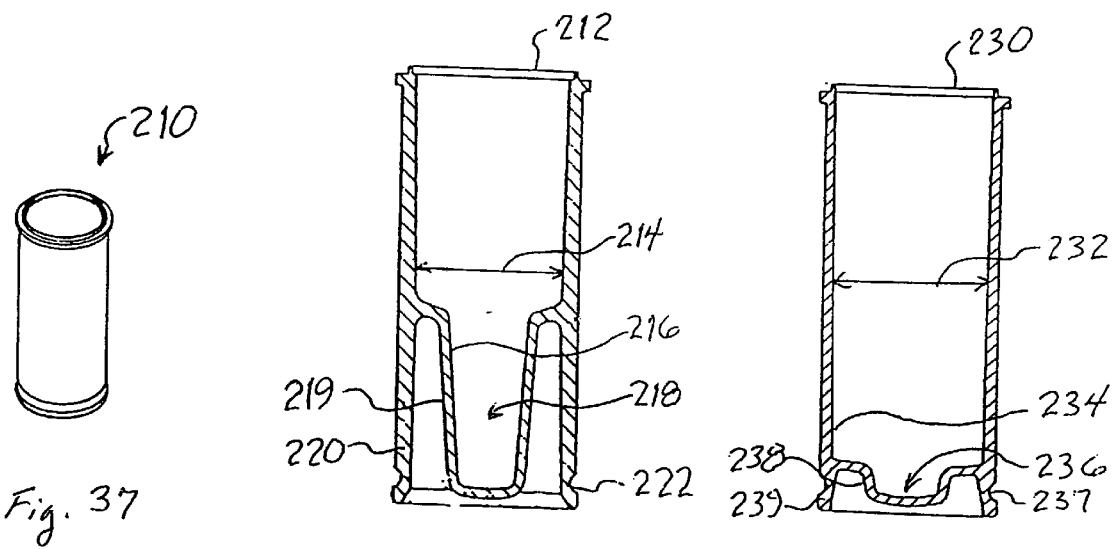
FIG. 37 illustrates a vial for use in conjunction with the vial carrier of FIG. 26.
FIG. 38 is a cross-sectional view of a first embodiment of the vial of FIG. 37.
FIG. 39 is a cross-sectional view of a second embodiment of the vial of FIG. 37.

Each compartment 202 is configured to accept a vial 210 such as that shown in FIG. 37. Any one of plural vial types may be utilized in each of the carrier compartments 202, though each vial type has the same outside appearance and features. Thus, vials having differing capacities may be employed in the present system. In one embodiment, the carrier 200 and the vials 210 are fabricated from high-density polyethylene (HDPE).

In FIG. 38, an allergen vial 212 having a 10 dose capacity is illustrated. The interior diameter 214 of the ten dose vial 212 narrows part-way down the inside wall 216 of the vial 212, forming a well region 218. A probe (not shown) associated with the automated assay instrument is lowered to a point proximate the bottom of the well region 218. This well region 218 facilitates the complete aspiration of the reagent contained within the vial 212. Locating features (not shown), such as fins extending between the well region exterior wall 219 and the outer wall 220 of the vial 212, cooperate with guides 201 (FIG. 30) which protrude up from the bottom of each compartment. The locating features thus enable the vial to be properly aligned within the compartment.

A circumferential groove 222 is formed along the outer surface of the vial 212, proximate a lower edge thereof. This groove 222 is utilized in maintaining the vial 212 within the respective carrier compartments 202, as described subsequently. The upper edge of the vial 212 is formed for the purpose of accepting an integral combination of a seal 224 (FIG. 40) and an overlying cap 228 (FIG. 41). The pierceable seal 224 and cap 228 are employed to enable selective aspiration of vial contents, while minimizing evaporation after initial aspiration.

In FIG. 39, an allergen vial 230 having a fifty dose capacity is illustrated. In contrast to the ten dose vial 212, the fifty dose vial 230 interior diameter 232 does not narrow to a significant degree until proximate the lower extent of the interior wall 234 of the vial 230, where a shallow well 236 is formed, also for the purpose of enabling more complete aspiration of the reagent from the vial 230 via a probe extending down into the well region 236 from the instrument. Locating features (not shown), such as fins extending between the well region exterior wall 238 and the outer wall 239 of the vial 230, cooperate with the guides 201 previously described.

Externally, the fifty dose vial 230 has the same appearance as the ten dose vial 212. For instance, the lower extremity of the exterior wall of the fifty dose vial 230 has a circumferential groove 237, and the upper extent of the exterior wall is adapted to receive the same seal 224 and cap 228 as previously described.

The seal 224 is a provided as a pierceable material, capable of substantial self-healing subsequent to being pierced by a probe for reagent aspiration. For this purpose, the seal is preferably formed of a silicone-type material, such as Elaslosil LR 3003/70 B (Wacker Chemie GmbH) or Silopren LSR 4070 (Bayer). The cap 228 is preferably formed of a non-reactive, rigid plastic material such as high-density polyethylene (HDPE). After application of a liquid-impermeable film 225, such heat-sealed SCOTCHPACK 300 (3M Corp.), the combination cap 228 and seal 224 are installed on the vial 210. These elements are depicted in FIG. 42, with the seal 224 installed on the underside of the cap 228.

Each vial 210 is preferentially provided with a label 240 such as that shown in FIG. 43. This label provides information to a user such as, for an allergen, lot number and expiration 241, allergen family (for instance, through a representative symbol) 242, allergen name 243, human-readable identification code 244, machine readable identification code 245, and source of origin, appropriate warnings and use instructions 247. The identification code employed may be in the form of a bar-code having an associated alpha-numeric field for human interpretation. The identification code is provided in a particular orientation, for the purpose of facilitating machine recognition of the code once the vial 210 is properly installed within one of the vial compartments 202 in the carrier 200.

Again with reference to FIG. 29, each compartment in the carrier is provided with a slot or window 250 in a side wall thereof. In addition, referring to FIG. 27, the carrier 210 is preferably provided with a notch 252 on an opposite wall thereof. When a vial 210, bearing a label 240 such as that illustrated in FIG. 43, is installed in a respective carrier compartment 202 and then rotated to the proper position through the use of the locating features previously described, the machine readable identification code 245 will appear in the slot 250 (see FIG. 36), and the indication of allergen family 242 will appear in the notch 252 in the opposite wall of the carrier 210 (see FIG. 34). These label elements thus act as visual cues to the user for proper installation of a vial in a respective compartment. Note that FIGS. 34 and 36 omit certain structural details of the carrier for the sake of simplicity.

At the lower reach of each vial compartment 202 in the carrier, at least one indexing member 253 protrudes towards the space to be occupied by a respective vial. When the vial 210 is installed in the compartment 202, the indexing member(s) 253 is temporarily deflected away from the vial 210 by the lower edge of the vial. Then, as the bottom edge of the vial 210 reaches the lower extent of the compartment 202, the indexing member 253 extends into the respective circumferential groove 222, 238 of the vial, holding the vial in place within the compartment. In one embodiment of the presently disclosed carrier, a portion 255 of the bottom of each compartment 202 is cut away (see FIG. 31), such that a portion of the bottom surface of an installed vial is exposed. This enables a user to provide upward pressure against the bottom of the vial in order to overcome the retentive force supplied by the indexing member 253 and extract the vial from the compartment.

Once the compartments 202 of a vial carrier 200 have been populated by respective vials 210, it is necessary to provide the instrument with the configuration of the carrier 200. This is achieved either automatically or manually. To be performed automatically, the instrument into which the carrier is installed is provided with an interface capable of interpreting the indicia associated with the carrier, each compartment, and the vials installed within the compartments. For instance, if the indicia are provided in bar-code format, a bar-code reader, which may be either hand-held or fixed, is utilized.

Figure 46:
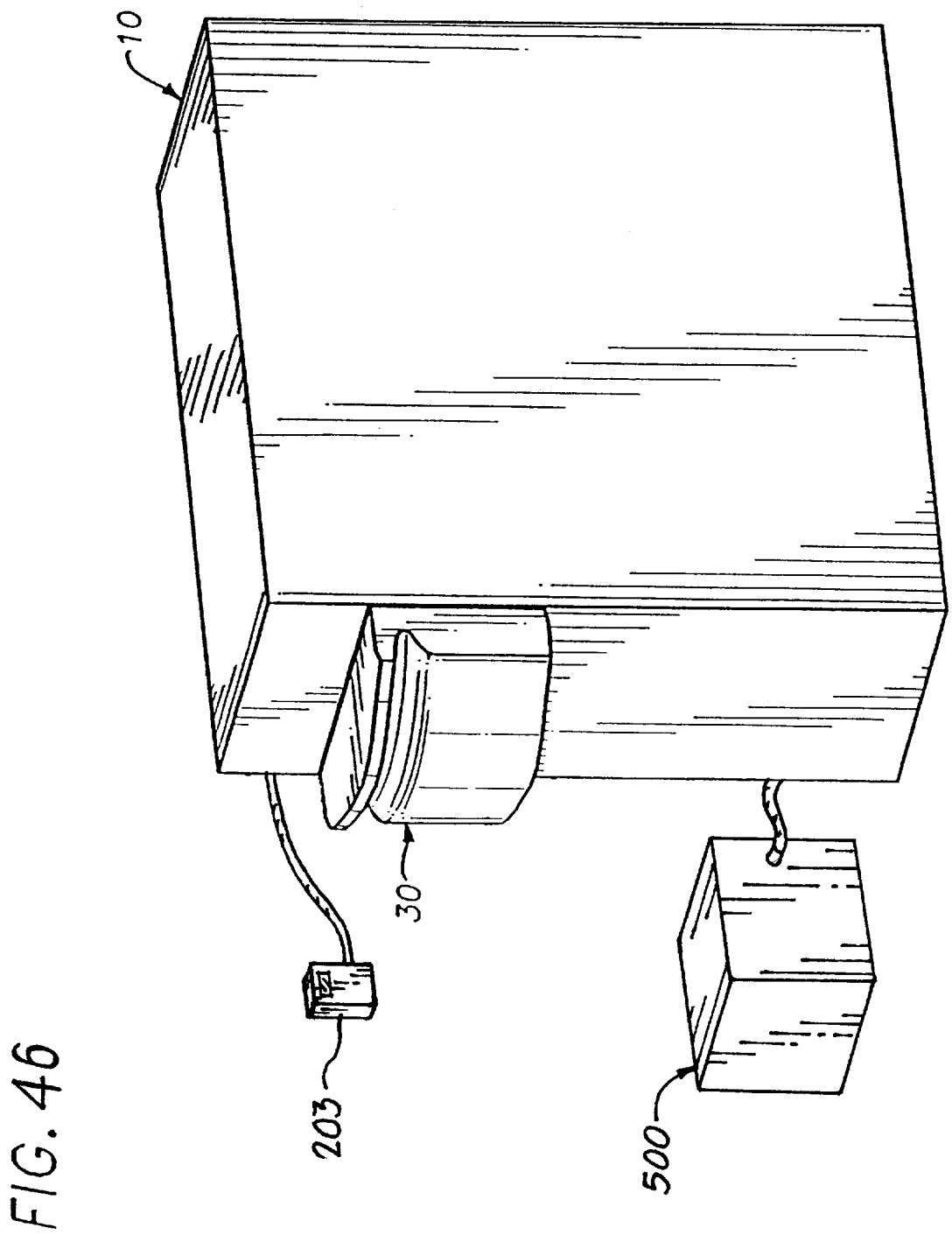
FIG. 46 illustrates a bar code scanner and controller for use in conjunction with the automated analyzer system of FIG. 1.

In one embodiment of the presently disclosed invention, a hand-held bar-code scanner 203 (FIG. 46) is passed across the side of the carrier 200 illustrated in FIG. 36 from a front end 206 first to a handle end 204. In this manner, carrier side indicia 207 are scanned last, identifying to the instrument which carrier data has been provided. First, a bar-code 208 identifying the first compartment 202 is scanned, followed by the bar-code 245 of the vial 210 installed in the first compartment 202. The latter two scans are then repeated sequentially for the remaining compartments 202 and associated vials 210. The same procedure is followed for an embodiment employing a fixed bar-code scanner associated with the automated analyzer system 10, wherein the populated vial carrier 200 is passed in front of the scanner in a predetermined manner. Other alternative embodiments are capable of recognizing which compartments are which within a specific carrier, and are thus capable of accommodating a carrier scanned in an order other than that just described.

Further embodiments employ alternative indicia and recognition means, such as magnetic stripes and readers, etc. Additionally, human-readable indicia 211 identifying the carrier may be provided on the carrier handle end 204 and on the side of the carrier side, proximate the carrier side indicia 207.

Information characterizing a configured carrier 200 to the system 10 is entered manually in a further embodiment. This embodiment can be combined with the embodiment providing automated indicia recognition means, such as the bar-code reader. Manual data entry may be necessary in certain circumstances, such as when a bar-code on a carrier 200 or vial 210 has been damaged and automated data retrieval is not possible. For this reason, an interface such as a keyboard or touch sensitive display screen is provided in this embodiment to accept manual entry of configuration data.

Whether the automated analyzer system 10 employs automated and/or manual configuration collection information, the system 10 preferentially provides configuration status to a user in a further embodiment. For instance, a display (not shown) associated with the system 10 provides a scan status display, such as that shown in FIG. 44. A user can command the system to prepare to receive scanned configuration data by placing the system 10 into a "ready to scan" state. As each indicia on the carrier 200 or associated vials 210 is successfully scanned, an indication, such as "OK", appears on the scan status display in the appropriate location. If the system is unable to properly associate scanned data with a model of the carrier it is building, an error indication is displayed at the point where the error was detected.

The system 10 comprises a programmable processor 500 (FIG. 46) and associated memory for receiving the carrier configuration information for each of the carriers 200 to be installed in the system 10, and for associating that information with the physical location where each carrier is ultimately installed in the enclosure 40. As known to one skilled in the art, various elements can be used to realize this processor 500, such as a microcontroller. This configuration information enables the system 10 to know where each vial is in the enclosure 40, thus enabling automated aspiration of reagent from the vials in the course of performing various assays, as previously described. Once configuration information for a particular carrier has been stored in system 10 memory, the configuration may be edited using, for instance, a system keyboard.

Once the system 10 has been provided with the configuration of a carrier 200, the carrier 200 is ready for installation into the reagent enclosure 40 through the use of a slide 50. The slides are accessible once the reagent door 34 has been opened, exposing the reagent enclosure 40. Each carrier 200 has an underside configuration substantially similar to that of the reagent pack 62, as previously described, for the purpose of properly and securely locating the carrier 210 above the respective slide 50. In a preferred embodiment, however, each carrier is provided with a downwardly extending feature 257 (FIG. 28) below the handle end of the carrier. This feature 257 is provided with a concave depression which cooperates with a convex retention feature 259, such as illustrated in one embodiment of the slide 50 of FIG. 4. As above, the accessibility of a particular slide 50 is indicated through an associated LED 66. If the associated LED is illuminated, it indicates that the reagent pack 62 or vial carrier 200 installed on that slide 50 is being accessed, or is about to be accessed, and is therefore not capable of being withdrawn at that time.

Figure 45:
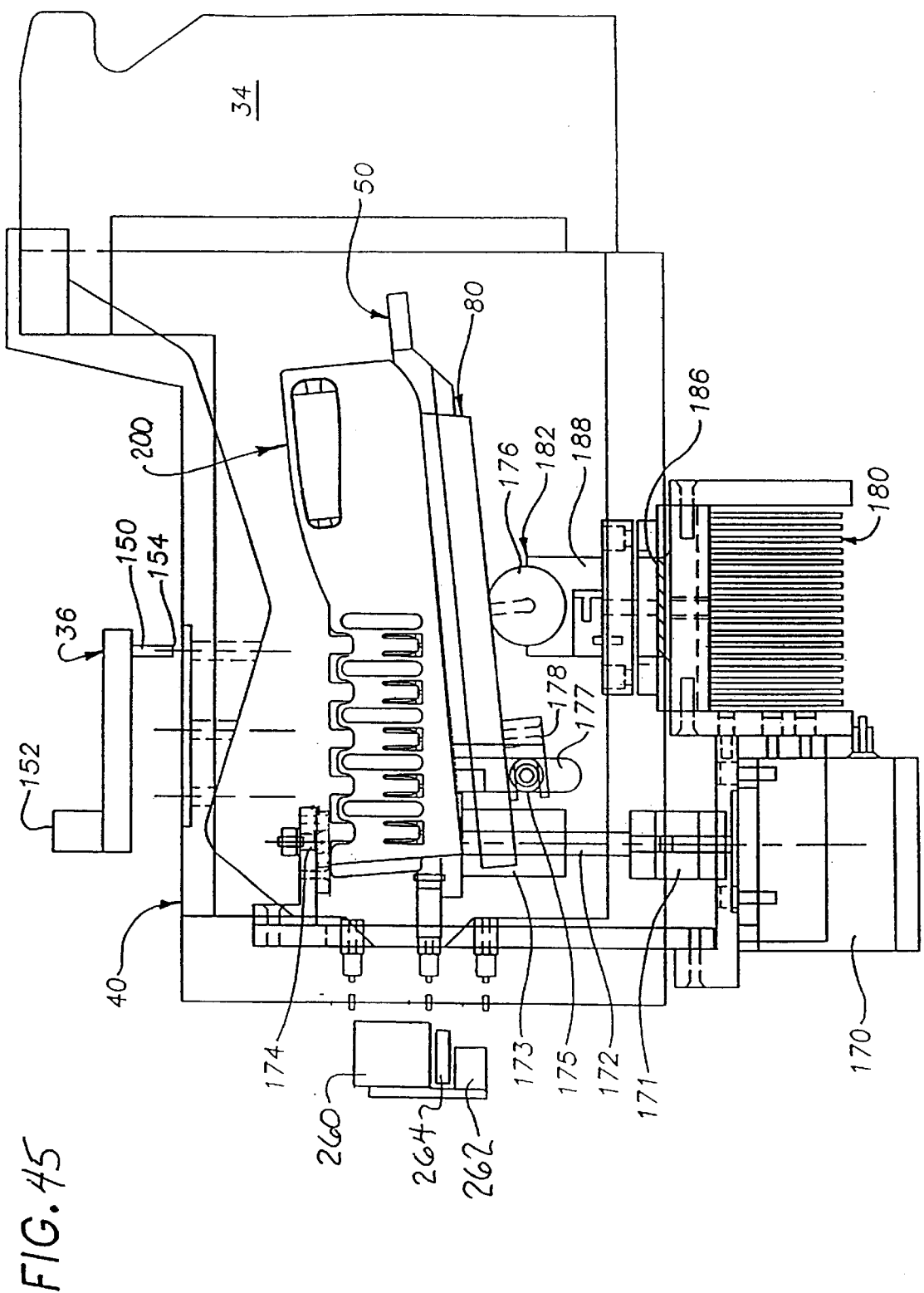
FIG. 45 illustrates the vial carrier of FIG. 26 installed within the enclosure of FIG. 16 and illustrating an indicia reading device proximate thereto.

The carrier side indicia 207 has already been scanned in order to identify the carrier to the system 10 during carrier configuration. Each carrier has an identical carrier indicia 209 disposed on the front end 206 of the carrier 200. With reference to FIG. 45, an automated indicia reading device 260, such as a bar code reader, is translated in a first embodiment horizontally along the rear of the enclosure 40 by a motor 262 such as a stepper motor and supported by a horizontal element 264 such as a slide. The indicia reading device 260 is thus capable of identifying each carrier 200 or reagent pack 62 installed in the enclosure via recognition of the carrier front end indicia 209. The system, having been provided with the vial configuration of a carrier 200, is then capable of locating any vial located within the enclosure 40 for automated probe manipulation and aspiration.

In one embodiment of the automated analyzer system as presently disclosed, both reagent packs 62 and vial carriers 200 are employed in the reagent handling system 30, depending upon the requirements of the assays to be performed.

These and other examples of the invention illustrated above are intended by way of example and the actual scope of the invention is to be determined from the following claims.

What is claimed is:

1. A liquid handling system, comprising:

an enclosure;

plural liquid-bearing vials;

plural vial carriers, each configured for receiving said plural vials in respective compartments of each carrier, said carriers disposable within said enclosure;

unique carrier indicia associated with each of said plural vial carriers;

unique compartment indicia associated with each of said plural compartments;

unique vial indicia associated with each of said plural vials;

liquid extraction apparatus associated with said enclosure for selectively extracting a quantity of liquid from a selected one of said vials once said selected vial is received within one of said carriers and disposed within said enclosure;

a first indicia data gathering element for identifying said compartment indicia, said vial carrier indicia and said vial indicia;

a second indicia data gathering element associated with said enclosure for identifying said vial carrier indicia; and a processing element in association with said liquid extraction apparatus and said first and second indicia data gathering elements for controlling said liquid extraction apparatus in accordance with said identifications.

2. The system of claim 1, wherein said enclosure further comprises a tray for receiving said carriers, and means for inclining said tray about a first axis of said tray once said carriers have been received on said tray.

3. The system of claim 1, wherein each of said vial carriers further comprises a retention element associated with each of said compartments for releasably retaining a vial disposed therein in a desired orientation.

4. The system of claim 3, wherein said unique vial indicia is further for identifying the contents of the respective vial.

5. The system of claim 4, wherein said first indicia data gathering element enables said processing element to uniquely identify the vial carrier and compartment in which each of said plural vials is disposed, and said second indicia data gathering element enables said processing element to uniquely locate each carrier disposed within said enclosure, whereby said processing element is adapted for commanding said liquid extraction apparatus to extract a desired liquid from any vial in any carrier within said enclosure.

* * * * *